United States Patent [19]

Krause et al.

[11] 4,386,007

[45] May 31, 1983

[54] LIQUID CRYSTALLINE NAPHTHALENE DERIVATIVES

[75] Inventors: Joachim Krause, Dieburg; Michael Römer, Rodgau; Ludwig Pohl, Darmstadt, all of Fed. Rep. of Germany

[73] Assignee: Merck Patent Gesellschaft mit beschrankter Haftung, Darmstadt, Fed. Rep. of Germany

[21] Appl. No.: 213,517

[22] Filed: Dec. 5, 1980

[30] Foreign Application Priority Data

Dec. 6, 1979 [DE] Fed. Rep. of Germany ....... 2949080

[51] Int. Cl.³ .......................... C09K 3/34; G02F 1/13; C07C 43/20; C07C 13/48; C07C 23/36; C07C 25/18; C07C 69/14; C07C 69/24

[52] U.S. Cl. .......................... 252/299.62; 252/299.5; 260/463; 260/465 C; 260/465 D; 260/465 G; 260/465.3; 350/350 R; 560/141; 568/632; 568/929; 568/941; 568/942; 570/129; 570/130; 570/183; 570/187; 585/20; 585/21

[58] Field of Search .............. 568/632, 929, 941, 942; 260/463, 465 C, 465 D, 465 G, 465.3; 560/141; 585/20, 21; 570/129, 187, 130, 183; 252/299.62, 299.63, 299.5; 350/350 R

[56] References Cited

U.S. PATENT DOCUMENTS

| | | | |
|---|---|---|---|
| 4,009,934 | 3/1977 | Goodwin et al. | 252/299.62 |
| 4,113,647 | 9/1978 | Coates et al. | 252/299.62 |
| 4,119,558 | 10/1978 | Coates et al. | 252/299.62 |
| 4,130,502 | 12/1978 | Eidenschink et al. | 252/299.63 |
| 4,154,697 | 5/1979 | Eidenschink et al. | 252/299.63 |
| 4,198,130 | 4/1980 | Boller et al. | 252/299.5 |
| 4,211,666 | 7/1980 | Inukai et al. | 252/299.6 |
| 4,219,256 | 8/1980 | Gray et al. | 252/299.62 |
| 4,229,315 | 10/1980 | Krause et al. | 252/299.63 |
| 4,261,651 | 4/1981 | Gray et al. | 252/299.62 |
| 4,302,352 | 11/1981 | Eidenschink et al. | 252/299.63 |
| 4,331,552 | 5/1982 | Eidenschink et al. | 252/299.6 |
| 4,340,498 | 7/1982 | Sugimori | 252/299.62 |

FOREIGN PATENT DOCUMENTS

| | | | |
|---|---|---|---|
| 164588 | 3/1953 | Australia | 568/633 |
| 25598 | 12/1980 | European Pat. Off. | 585/21 |
| 56-46855 | 4/1981 | Japan | 252/299.62 |
| 56-68636 | 6/1981 | Japan | 568/931 |
| 56-108740 | 8/1981 | Japan | 252/299.62 |
| 56129288 | 10/1981 | Japan | 252/299.62 |
| 2082179 | 3/1982 | United Kingdom | 252/299.62 |
| 2090593 | 7/1982 | United Kingdom | 252/299.62 |

OTHER PUBLICATIONS

Gray, G. W., et al., Liquid Crystals & Plastic Crystals, vol. 1, Ellis Horwood Ltd., England, pp. 136–137.
Gray, G. W., et al., Mol. Cryst. Liq. Cryst., vol. 53, pp. 147–166 (1979).
Coates, D., et al., Mol. Cryst. Liq. Cryst., vol. 37, pp. 249–262, (1976).
Lauk, U., et al., Helvetica, Chimica Acta, vol. 64, pp. 1847–1848 (1981).

*Primary Examiner*—Teddy S. Gron
*Attorney, Agent, or Firm*—Millen & White

[57] ABSTRACT

Liquid crystalline naphthalene derivatives of the formula

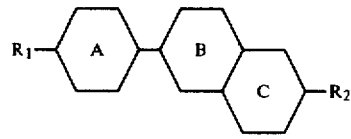

wherein ring A is 1,4-phenylene, trans-1,4-cyclohexylene or 1,4-cyclohex-1-enylene and ring system BC is 2,6-naphthylene, 3,4-dihydro-2,6-naphthylene or 1,2,3,4-tetrahydro-2,6-naphthylene, with the proviso that A is not 1,4-phenylene when BC is 2,6-naphthylene; and $R_1$ and $R_2$, which are identical or different, are each alkyl of up to 8 C atoms or, when the rings to which they are bonded are aromatic, also can be alkoxy, alkanoyloxy or alkoxycarbonyloxy having up to 8 C atoms in each case; or one of $R_1$ and $R_2$ also can be CN, halogen, $CF_3$ or $NO_2$ are valuable components for liquid crystalline dielectrics.

4 Claims, No Drawings

LIQUID CRYSTALLINE NAPHTHALENE DERIVATIVES

BACKGROUND OF THE INVENTION

The properties of nematic or nematic-cholesteric liquid-crystalline materials are increasingly being utilized for electro-optical display elements by taking advantage of significant changes in the optical properties of the latter, such as light absorption, light scattering, birefringence, reflectance or color, under the influence of electric fields. The functioning of display elements of this type is based, for example, on the phenomena of dynamic scattering, the deformation of aligned phases, the Schadt-Helfrich effect in the twisted cell or the cholesteric-nematic phase transition.

For the technical application of these effects to electronic components, liquid-crystalline dielectrics are required which must fulfill a large number of requirements. Their chemical resistance to moisture, air and physical influences, such as heat, radiation in the infrared, visible and ultraviolet ranges, and continuous and alternating electric fields, is of particular importance. Industrially usable liquid-crystalline dielectrics are also required to have a liquid-crystalline mesophase in the temperature range from at least +10° C. to +50° C., preferably from 0° C. to 60° C., and the lowest possible viscosity at room temperature, which preferably should not exceed $70 \times 10^{-3}$ Pa.s. Finally, they must not have any characteristic absorption in the range of visible light, i.e., they must be colorless.

A number of liquid-crystalline compounds have already been disclosed, which fulfill the stability demands made for dielectrics intended for electronic components, and which are also colorless. These include, in particular, the p,p'-disubstituted phenyl benzoates described in German Offenlegungsschrift No. 2,139,628 and the p,p'-disubstituted phenylcyclohexane derivatives described in German Offenlegungsschrift No. 2,636,684. In these two classes of compounds, and also in other known series of compounds with a liquid-crystalline mesophase, there are no individual compounds which form a liquid-crystalline nematic mesophase in the required temperature range from 10° C. to 60° C. As a rule, mixtures of two or more compounds are therefore prepared, in order to obtain substances which can be used as liquid-crystalline dielectrics. For this purpose, at least one compound having a low melting point and clear point is usually mixed with another compound having a markedly higher melting point and clear point. This normally produces a mixture, the melting point of which is below that of the lower-melting component, while the clear point is between the clear points of the components. It is, however, not easy to prepare optimum dielectrics in this way, since the components having the high melting points and clear points frequently also impart a high viscosity to the mixtures. As a result, the switching times of the electro-optical display elements produced with these mixtures are extended in an undesirable manner.

SUMMARY OF THE INVENTION

Accordingly, it is an object of this invention to provide liquid-crystalline dielectrics which have a nematic phase within the required temperature range and, which make switching times possible in liquid crystal cells which are sufficiently short at room temperature.

Upon further study of the specification and appended claims, further objects and advantages of this invention will become apparent to those skilled in the art.

These objects have been achieved by providing naphthalene derivatives of formula (I)

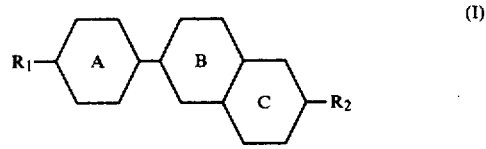

(I)

wherein ring A is 1,4-phenylene, trans-1,4-cyclohexylene or 1,4-cyclohex-1-enylene and ring system BC is 2,6-naphthylene, 3,4-dihydro-2,6-naphthylene or 1,2,3,4-tetrahydro-2,6-naphthylene, with the proviso that A is not 1,4-phenylene when BC is 2,6-naphthylene; and $R_1$ and $R_2$, which are identical or different, are alkyl of up to 8 C atoms or, when the rings to which they are bonded are aromatic, also are alkoxy, alkanoyloxy or alkoxycarbonyloxy of up to 8 C atoms in each case; or one of $R_1$ and $R_2$ is CN, halogen, $CF_3$ or $NO_2$.

These compounds are outstandingly suitable as components of liquid-crystalline dielectrics. In fact, these compounds display a surprisingly broad range of applications; depending on the nature of the rings and on the choice of substituents, the compounds of formula (I) can be used as base materials which exclusively or predominantly make up the composition of liquid-crystalline dielectrics; or compounds of formula (I) can also be added in smaller proportions of, for example, 2 to 45 percent by weight to liquid-crystalline base materials obtained from other classes of compounds. In this way, dielectrics can be prepared having a widened liquid-crystalline mesophase or the magnitude of the dielectric anisotropy of such a dielectric can be influenced.

By suitable choice of the substituents $R_1$ and $R_2$, the compounds of formula (I) can be used to prepare dielectrics having a pronounced positive dielectric anisotropy, for use in display elements based on the twisted nematic cell or the cholesteric-nematic phase transition. It is also possible to prepare dielectrics with a dielectric anisotropy which only slightly differs from zero or is even negative, the latter dielectrics being used in display elements based on dynamic scattering or on the deformation of aligned phases (DAP effect).

In the pure state, the compounds of formula (I) are colorless and chemically or photochemically extremely stable, and form nematic mesophases having an astonishingly low viscosity.

The present invention thus relates to naphthalene derivatives of formula (I) and to their use as components of liquid-crystalline dielectrics. Furthermore, the invention relates to liquid-crystalline dielectrics which contain at least one naphthalene derivative of formula (I), and to electro-optical display elements which are based on a liquid crystal cell containing a liquid-crystalline dielectric of this type.

DETAILED DISCUSSION

The naphthalene derivatives of this invention thus comprise 6-(trans-cyclohexyl)-napthalenes of formula (Ia)

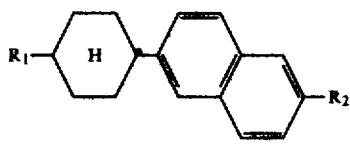

6-cyclohex-1-enylnaphthalenes of formula (Ib)

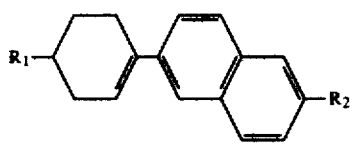

6-(trans-cyclohexyl)-3,4-dihydronaphthalenes of formula (Ic)

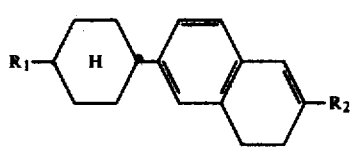

6-cyclohex-1-enyl-3,4-dihydronaphthalenes of formula (Id)

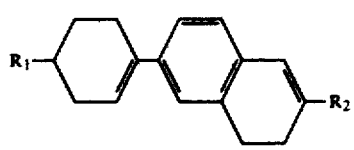

6-phenyl-3,4-dihydronaphthalenes of formula (Ie)

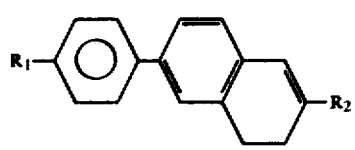

6-(trans-cyclohexyl)-1,2,3,4-tetrahydronaphthalenes of formula (If)

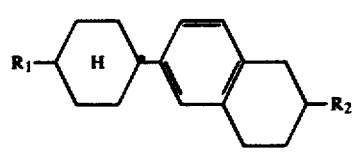

6-cyclohex-1-enyl-1,2,3,4-tetrahydronaphthalenes of formula (Ig)

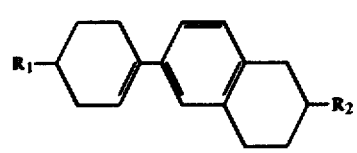

and 6-phenyl-1,2,3,4-tetrahydronaphthalenes of formula (Ih)

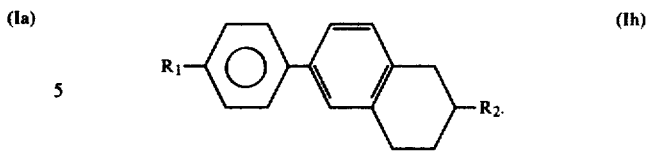

In all the compounds of formulae (Ia) to (Ih), $R_1$ and $R_2$ are as defined for formula (I). When, in these compounds, $R_1$ and $R_2$ denote alkyl groups R, alkoxy groups OR, alkanoyloxy groups OCOR or alkoxycarbonyloxy groups OCOOR, the alkyl portion R can be straight-chain or branched. When R is straight-chain, i.e., is methyl, ethyl, n-propyl, n-butyl, n-pentyl, n-hexyl, n-heptyl or, in alkyl or alkoxy groups, also n-octyl, the resultant compounds generally possess higher clear points than the compounds having branched wing groups $R_1$ and/or $R_2$. For this reason, usually only one of the wing groups $R_1$ and $R_2$ contains a branched carbon chain.

Compounds of formula (I), having a branched wing group $R_1$ or $R_2$, are occasionally important because of their higher solubility in the conventional liquid-crystalline base materials, but particularly as chiral doping substances if they possess optical activity due to the chain branching. Such branched substituents generally do not contain more than one chain branching. Preferred branched radicals R are those in which a methyl or ethyl group is located in the 2- or 3-position on a relatively long carbon chain, for example, 2-methylpropyl, 2-methylbutyl, 3-methylbutyl, 2-methylpentyl, 3-methylpentyl, 2-ethylhexyl or 2-methylhexyl. If one of the wing groups $R_1$ or $R_2$ is CN, $NO_2$, halogen or $CF_3$, the resultant compounds possess, as a rule, a more or less pronounced positive dielectric anisotropy. Among the compounds of formula (I) in which both $R_1$ and $R_2$ contain carbon chains, those are preferred in which the wing groups contain not more than 14, in particular only up to 12, C atoms in total.

The groups compiled in the following table are particularly preferred in compounds of formula (I), within the scope of the present invention:

| Structural formula | $R_1$ | $R_2$ |
|---|---|---|
| (Ia) | alkyl (1–6 C atoms) | alkyl, alkoxy, alkanoyloxy (each having up to 6 C atoms), halogen, CN |
| (Ib) | alkyl (1–6 C atoms) | alkyl, alkoxy, alkanoyloxy (each having up to 6 C atoms), CN |
| (Ic) | alkyl (1–8 C atoms) | alkyl (1–8 C atoms) |
| (Id) | alkyl (1–6 C atoms) | alkyl (1–8 C atoms) |
| (Ie) | alkyl, alkoxy, alkanoyloxy (each having up to 6 C atoms), CN | alkyl (1–8 C atoms) |
| (If) | alkyl (1–8 C atoms) | alkyl (1–6 C atoms) |
| (Ig) | alkyl (1–6 C atoms) | alkyl (1–6 C atoms) |
| (Ih) | alkyl, alkoxy, alkanoyloxy (each having up to 6 C atoms), CN, halogen, $CF_3$ | alkyl (1–8 C atoms). |

The compounds of this invention can be prepared in a manner which is conventional for substances of this type.

For example, compounds of formula (Ib), in which $R_2$ is alkyl or alkoxy can be obtained by reacting a Grignard compound of formula (II)

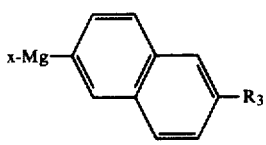
(II)

wherein x is chlorine or bromine and $R_3$ is alkyl or alkoxy of up to 8 C atoms, with a cyclohexanone derivative of formula (III)

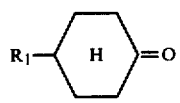
(III)

wherein $R_1$ is alkyl of up to 8 C atoms, hydrolyzing the reaction product in a manner known per se and splitting off water from the resultant alcohol of formula (IV)

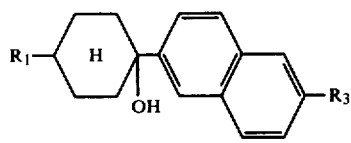
(IV)

wherein $R_1$ and $R_3$ have the meaning indicated above, in a manner known per se, for example by treatment with a mineral acid, carboxylic acid or sulfonic acid.

To prepare compounds of formula (Ib), in which $R_2$ is other than alkyl or alkoxy, the alkoxy compound can be subjected to ether cleavage and the 6-(4-alkylcyclohex-1-enyl)-2-hydroxynaphthalene thus obtained is converted to the desired derivatives by reactions known per se. Thus, alkanoyloxy radicals or alkoxycarbonyloxy radicals are introduced by reaction with the corresponding carboxylic acid halides or alkoxycarbonyl halides; a halogen radical $R_2$ is introduced by reaction with a thionyl halide or phosphorus oxyhalide. From the compounds of formula (I), in which $R_2$ denotes halogen, preferably chlorine or bromine, the corresponding carbonitriles ($R_2$=CN) are prepared, for example, by reaction with copper-I cyanide in pyridine. The carbonitriles, in turn, can be converted to the trifluoromethyl derivatives ($R_2$=CF$_3$) by saponification to the carboxylic acid and subsequent reaction with sulfur tetrafluoride. The nitro compounds of formula (I) are prepared, for example, from the 2-hydroxynaphthalenes by reaction with ammonium sulfite under elevated pressure and at elevated temperature (Bucherer reaction) to give 2-amino-naphthalene derivatives, diazotization of the latter and reaction with sodium nitrite in the presence of copper-I compounds.

The compounds of formula (Ia) are prepared, for example, by hydrogenating a corresponding compound of formula (Ib), wherein $R_2$ is alkyl or alkoxy, and isolating the trans-isomer in the conventional manner, for example, by crystallization or chromatography, from the resulting mixture of cis/trans-isomers, if appropriate after a preceding equilibration, for example, by treatment with potassium tert-butylate in alcohol. Compounds of formula (Ia), in which $R_2$ is other than alkyl or alkoxy, can be obtained from the alkoxy compound in the manner indicated above for the analogous compounds of formula (Ib).

The compounds of formula (Ic) can be prepared by hydrogenating a 6-(4-trans-alkylcyclohexyl)-2-hydroxynaphthalene over platinum oxide under elevated pressure and at elevated temperature to give 6-(4-trans-alkylcyclohexyl)-1,2,3,4-tetrahydronaphthalen-2-one, reacting the latter in ether with an alkylmagnesium halide compound and dehydrating the 6-(4-trans-alkylcyclohexyl)-1,2,3,4-tetrahydro-2-alkyl-2-hydroxynaphthalene, obtained after hydrolysis, in a manner known per se, for example using p-toluenesulfonic acid in acetone. A compound of the formula (Ic), thus obtained, can also be readily converted to a compound of formula (If) by hydrogenation over palladium-on-active charcoal under standard conditions.

To prepare a compound of formula (Ig), a compound of formula (If) is slowly reacted at moderate temperature with N-bromosuccinimide in carbon tetrachloride. Hydrogen bromide is split off the 6-(4-alkyl-1-bromocyclohexyl)-2-alkyl-1,2,3,4-tetrahydronaphthalene, thus obtained, by treatment with triethylamine in an inert solvent, such as, for example, toluene. By reacting a compound of formula (If) with excess N-bromosuccinimide at elevated temperature, if appropriate in the presence of catalytic amounts of a free-radical former, such as dibenzoyl peroxide, 6-(4-alkyl-1-bromocyclohexyl)-2-alkyl-1-bromo-1,2,3,4-tetrahydronaphthalene is obtained, and this is converted to a compound of formula (Id) by dehydrobromination, for example, with triethylamine.

The compounds of the formula (Ih) can be obtained, for example, by introducing a hydroxymethyl group into a biphenyl ketone of formula (V)

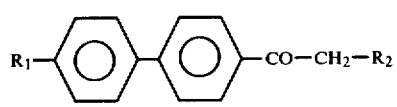
(V)

by reaction with sodium and paraformaldehyde in tetrahydrofuran and, in the compound of the formula (VI)

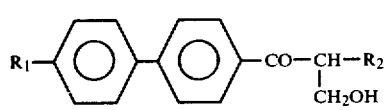
(VI)

thus obtained, reducing the carbonyl group to the methylene group, for example, by hydrogenation over palladium-on-active charcoal under standard conditions, and subsequently converting the alcohol (VII)

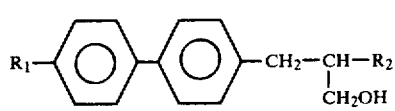
(VII)

thus prepared, by sequential reaction with p-toluenesulfochloride in tetrahydrofuran and potassium cyanide in dimethylformamide into the nitrile (VIII)

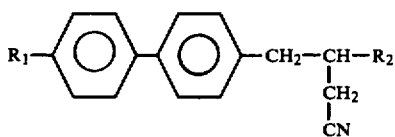

(VIII)

which is then saponified to the carboxylic acid (IX)

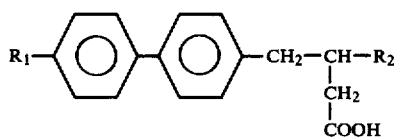

(IX)

for example by warming with aqueous potassium hydroxide solution. This carboxylic acid (IX) is then cyclized in the conventional manner, in the presence of an acid catalyst, for example, polyphosphoric acid, to give 6-phenyl-1,2,3,4-tetrahydronaphthalene (Ih); if desired, an undesired radical $R_1$ can be exchanged for a desired radical in the manner described above. 6-Phenyl-3,4-dihydronaphthalenes (Ie) can be prepared by reaction of 6-phenyl-1,2,3,4-tetrahydronaphthalenes (Ih) with N-bromosuccinimide and subsequent dehydrobromination.

The majority of the starting materials for the above-described syntheses of the compounds of this invention are described in the literature; where they are not explicitly mentioned in the literature, for example, higher homologs of the biphenyl ketones (V) ($R_1$, $R_2$=pentyl, hexyl and the like), they can be prepared without difficulty using the processes described therein for the preparation of the base compounds.

The liquid-crystalline dielectrics of this invention consist of two or more components, including at least one component of formula (I); dielectrics of this invention can, however, also consist exclusively of compounds of formula (I), disregarding doping substances or additives, which may additionally be present, if appropriate, and which do not necessarily have to be liquid-crystalline themselves. Other components which may be used are preferably nematic or nematogenic substances from the conventional series of azobenzenes, azoxybenzenes, biphenyls, Schiff bases, in particular benzylidene derivatives, phenyl benzoates, phenylpyrimidines, phenylcyclohexanes, optionally halogenated stilbenes, diphenylacetylene derivatives, diphenylnitrones and substituted cinnamic acids. The most important compounds which can be used as such additional components, can be characterized by formula (X):

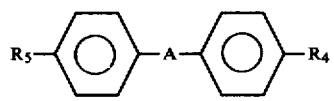

(X)

wherein A is:

| | |
|---|---|
| —CH=CH— | —O—CO—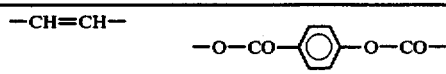—O—CO— |
| —CX=CH— | —CO—O—⌬—CO—O— |
| —CH=CX— | —⌬—CO—O— |
| —C≡C— | —⌬—O—CO— |
| —N=N— | —⌬—CO—S— |
| —N(O)=N— | —⌬—S—CO— |
| —N=N(O)— | —CH=N— |
| —O—CO— | —N=CH— |
| —CO—O— | —CH=N(O)— |
| —S—CO— | —N(O)=CH— |
| —CO—S— | —⌬— or a C—C single bond. |

Further possible components of the dielectrics of this invention are those compounds of formula (X), in which one or more phenyl rings are replaced by a corresponding number of trans-cyclohexyl rings; one of these rings can also be a 2,5-disubstituted pyrimidine ring.

X is halogen, preferably Cl, or —CN. $R_5$ and $R_4$ are identical or different and can be alkyl, alkoxy, alkanoyl, alkanoyloxy or alkoxycarbonyloxy radicals of up to 18, preferably up to 8, C atoms; moreover, one of these radicals can also be —CN, —NC, $NO_2$, $CF_3$ or halogen.

In most of these compounds, $R_5$ and $R_4$ are preferably different, one of the radicals being an alkyl or alkoxy group in most cases. A large number of other variants of the envisaged substituents, however, are also common. Many such substances are commercially available.

The dielectrics of this invention contain as a rule at least 30, preferably 50–99, in particular 60–98, percent by weight of the compounds of formula (I) and, if appropriate, (X). Of this, at least 5 percent by weight, in most cases even 10 or more percent by weight, preferably is accounted for by one or more compounds of formula (I). The invention also comprises those liquid-crystalline dielectrics, to which only less than 5 percent by weight, for example 0.1 to 3 percent by weight of one or more compounds of formula (I) have been added, for example, for doping purposes.

The preparation of the dielectrics of this invention is carried out in a manner conventional per se. As a rule, the desired amount of the components used in a smaller quantity is dissolved in the component representing the main constituent, advantageously at elevated temperature. If a temperature above the clear point of the main constituent is chosen for this, the completeness of the solution process can be observed with particular ease.

It is also possible, however, to mix solutions of the components of formula (I), and, if appropriate, (X), in a suitable organic solvent, for example, acetone, chloroform or methanol, and, after thorough mixing, to remove the solvent again, for example, by distillation under reduced pressure. Of course, it is necessary in this procedure to take care that no impurities or undesired doping substances are introduced by the solvent.

The liquid-crystalline dielectrics of this invention can be modified by suitable additives in such a way that they can be used in all hitherto disclosed types of liquid crystal display elements. Additives of this type are known to those skilled in the art and are extensively described in the relevant literature. For example, substances can be added for varying the dielectric anisotropy, the viscosity, the conductivity and/or the orientation of the nematic phases. Substances of this type are described, for example, in German Offenlegungsschriften Nos. 2,209,127; 2,240,864; 2,321,632; 2,338,281 and 2,450,088.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point, and c.p. denotes the clear point, of a liquid-crystalline substance in degrees Centigrade; boiling points are marked b.p.

EXAMPLE 1

A solution of 18 g of 4-n-hexylcyclohexane in 35 ml of tetrahydrofuran is added dropwise, at 25° to 30°, over the course of one hour to a solution of hexyloxynaphthyl-magnesium bromide, prepared from 31 g of 6-bromo-2-hexyloxynaphthalene and 4 g of magnesium turnings in 160 ml of tetrahydrofuran. The reaction mixture is heated to a boil for a further 2 hours and then, after cooling, poured into a solution of 15 ml of concentrated hydrochloric acid in 350 ml of ice water. After the addition of 100 ml of diethyl ether, the phases are separated and the aqueous phase is extracted by shaking twice more with 75 ml of diethyl ether each time. The combined ether phases are washed with 5% strength sodium bicarbonate solution and then with water, dried over sodium sulfate and evaporated. The residue is dissolved in 100 ml of acetone and, after the addition of 6 g of p-toluenesulfonic acid, heated to the boil for 30 minutes. After cooling to −5°, the 6-(4-n-hexylcyclohex-1-enyl)-2-n-hexyloxynaphthalene, which has crystallized out, is filtered off and recrystallized from acetone; m.p. 72°, c.p. 132°.

The following are prepared analogously:
6-(4-methylcyclohex-1-enyl)-2-methoxy-naphthalene,
6-(4-ethylcyclohex-1-enyl)-2-methoxy-naphthalene,
6-(4-n-propylcyclohex-1-enyl)-2-methoxy-naphthalene,
6-(4-n-butylcyclohex-1-enyl)-2-methoxy-naphthalene,
6-(4-n-pentylcyclohex-1-enyl)-2-methoxy-naphthalene,
6-(4-n-hexylcyclohex-1-enyl)-2-methoxy-naphthalene,
6-(4-n-heptylcyclohex-1-enyl)-2-methoxy-naphthalene,
6-(4-n-octylcyclohex-1-enyl)-2-methoxy-naphthalene,
6-[4-(2-methylbutyl)-cyclohex-1-enyl]-2-methoxy-naphthalene,
6-(4-methylcyclohex-1-enyl)-2-ethoxy-naphthalene,
6-(4-ethylcyclohex-1-enyl)-2-ethoxy-naphthalene,
6-(4-n-propylcyclohex-1-enyl)-2-ethoxy-naphthalene,
6-(4-n-butylcyclohex-1-enyl)-2-ethoxy-naphthalene,
6-(4-n-pentylcyclohex-1-enyl)-2-ethoxy-naphthalene,
6-(4-n-hexylcyclohex-1-enyl)-2-ethoxy-naphthalene,
6-(4-n-heptylcyclohex-1-enyl)-2-ethoxy-naphthalene,
6-(4-n-octylcyclohex-1-enyl)-2-ethoxy-naphthalene,
6-[4-(2-methylbutyl)-cyclohex-1-enyl]-2-ethoxy-naphthalene,
6-(4-methylcyclohex-1-enyl)-2-n-propoxy-naphthalene,
6-(4-ethylcyclohex-1-enyl)-2-n-propoxy-naphthalene,
6-(4-n-propylcyclohex-1-enyl)-2-n-propoxy-naphthalene,
6-(4-n-butylcyclohex-1-enyl)-2-n-propoxy-naphthalene,
6-(4-n-pentylcyclohex-1-enyl)-2-n-propoxy-naphthalene,
6-(4-n-hexylcyclohex-1-enyl)-2-n-propoxy-naphthalene,
6-(4-n-heptylcyclohex-1-enyl)-2-n-propoxy-naphthalene,
6-(4-n-octylcyclohex-1-enyl)-2-n-propoxy-naphthalene,
6-[4-(2-methylbutyl)-cyclohex-1-enyl]-2-n-propoxy-naphthalene,
6-(4-methylcyclohex-1-enyl)-2-n-butoxy-naphthalene,
6-(4-ethylcyclohex-1-enyl)-2-n-butoxy-naphthalene,
6-(4-n-propylcyclohex-1-enyl)-2-n-butoxy-naphthalene, m.p. 79°, c.p. 127°;
6-(4-n-butylcyclohex-1-enyl)-2-n-butoxy-naphthalene,
6-(4-n-pentylcyclohex-1-enyl)-2-n-butoxy-naphthalene, m.p. 86°, c.p. 134°;
6-(4-n-hexylcyclohex-1-enyl)-2-n-butoxy-naphthalene,
6-(4-n-heptylcyclohex-1-enyl)-2-n-butoxy-naphthalene,
6-(4-n-octylcyclohex-1-enyl)-2-n-butoxy-naphthalene,
6-[4-(2-methylbutyl)-cyclohex-1-enyl]-2-n-butoxy-naphthalene,
6-(4-methylcyclohex-1-enyl)-2-n-pentyloxy-naphthalene,
6-(4-ethylcyclohex-1-enyl)-2-n-pentyloxy-naphthalene,
6-(4-n-propylcyclohex-1-enyl)-2-n-pentyloxy-naphthalene,
6-(4-n-butylcyclohex-1-enyl)-2-n-pentyloxy-naphthalene,
6-(4-n-pentylcyclohex-1-enyl)-2-n-pentyloxy-naphthalene,
6-(4-n-hexylcyclohex-1-enyl)-2-n-pentyloxy-naphthalene,
6-(4-n-heptylcyclohex-1-enyl)-2-n-pentyloxy-naphthalene,
6-[4-(2-methylbutyl)-cyclohex-1-enyl]-2-n-pentyloxy-naphthalene,
6-(4-methylcyclohex-1-enyl)-2-n-hexyloxy-naphthalene,
6-(4-ethylcyclohex-1-enyl)-2-n-hexyloxy-naphthalene,
6-(4-n-propylcyclohex-1-enyl)-2-n-hexyloxy-naphthalene,
6-(4-n-butylcyclohex-1-enyl)-2-n-hexyloxy-naphthalene,
6-(4-n-pentylcyclohex-1-enyl)-2-n-hexyloxy-naphthalene,
6-[4-(2-methylbutyl)-cyclohex-1-enyl]-2-n-hexyloxy-naphthalene,
6-(4-methylcyclohex-1-enyl)-2-n-heptyloxy-naphthalene,
6-(4-ethylcyclohex-1-enyl)-2-n-heptyloxy-naphthalene,
6-(4-n-propylcyclohex-1-enyl)-2-n-heptyloxy-naphthalene,
6-(4-n-butylcyclohex-1-enyl)-2-n-heptyloxy-naphthalene,
6-(4-n-pentylcyclohex-1-enyl)-2-n-heptyloxy-naphthalene,
6-[4-(2-methylbutyl)-cyclohex-1-enyl]-2-n-heptyloxy-naphthalene,
6-(4-methylcyclohex-1-enyl)-2-n-octyloxy-naphthalene, 6-(4-ethylcylohex-1-enyl)-2-n-octyloxy-naphthalene,
6-(4-n-propylcyclohex-1-enyl)-2-n-octyloxy-naphthalene,
6-(4-n-butylcyclohex-1-enyl)-2-n-octyloxy-naphthalene,
6-(4-n-pentylcyclohex-1-enyl)-2-n-octyloxy-naphthalene,
6-[4-(2-methylbutyl)-cyclohex-1-enyl]-2-n-octyloxy-naphthalene,
6-(4-methylcyclohex-1-enyl)-2-methyl-naphthalene,
6-(4-ethylcyclohex-1-enyl)-2-methyl-naphthalene,
6-(4-n-propylcyclohex-1-enyl)-2-methyl-naphthalene,
6-(4-n-butylcyclohex-1-enyl)-2-methyl-naphthalene,
6-(4-n-pentylcyclohex-1-enyl)-2-methyl-naphthalene,
6-(4-n-hexylcyclohex-1enyl)-2-methyl-naphthalene,
6-(4-n-heptylcyclohex-1-enyl)-2-methyl-naphthalene,
6-(4-n-octylcyclohex-1-enyl)-2-methyl-naphthalene,
6-[4-(2-methylbutyl)-cyclohex-1-enyl]-2-methyl-naphthalene,
6-(4-methylcyclohex-1-enyl)-2-ethyl-naphthalene,
6-(4-ethylcyclohex-1-enyl)-2-ethyl-naphthalene,
6-(4-n-propylcyclohex-1-enyl)-2-ethyl-naphthalene,
6-(4-n-butylcyclohex-1-enyl)-2-ethyl-naphthalene,
6-(4-n-pentylcyclohex-1-enyl)-2-ethyl-naphthalene,
6-(4-n-hexylcyclohex-1-enyl)-2-ethyl-naphthalene,
6-(4-n-heptylcyclohex-1-enyl)-2-ethyl-naphthalene,
6-(4-n-octylcyclohex-1-enyl)-2-ethyl-naphthalene,
6-[4-(2-methylbutyl)-cyclohex-1-enyl]-2-ethyl-naphthalene,
6-(4-methylcyclohex-1-enyl)-2-n-propyl-naphthalene,
6-(4-ethylcyclohex-1-enyl)-2-n-propyl-naphthalene,
6-(4-n-propylcyclohex-1-enyl)-2-n-propyl-naphthalene,
6-(4-n-butylcyclohex-1-enyl)-2-n-propyl-naphthalene,
6-(4-n-pentylcyclohex-1-enyl)-2-n-propyl-naphthalene,
6-(4-n-hexylcyclohex-1-enyl)-2-n-propyl-naphthalene,
6-(4-n-heptylcyclohex-1-enyl)-2-n-propyl-naphthalene,
6-(4-n-octylcyclohex-1-enyl)-2-n-propyl-naphthalene,
6-[4-(2-methylbutyl)-cyclohex-1-enyl]-2-n-propyl-naphthalene,
6-(4-methylcyclohex-1-enyl)-2-n-butyl-naphthalene,
6-(4-ethylcyclohex-1-enyl)-2-n-butyl-naphthalene,
6-(4-n-propylcyclohex-1-enyl)-2-butyl-naphthalene,
6-(4-n-butylcyclohex-1-enyl)-2n-butyl-naphthalene,
6-(4-n-pentylcyclohex-1-enyl)-2-n-butyl-naphthalene,
6-(4-n-hexylcyclohex-1-enyl)-2-n-butyl-naphthalene,
6-(4-n-heptylcyclohex-1-enyl)-2-n-butyl-naphthalene,
6-(4-n-octylcyclohex-1-enyl)-2-n-butyl-naphthalene,
6-[4-(2-methylbutyl)-cyclohex-1-enyl]-2-n-butyl-naphthalene,
6-(4-methylcyclohex-1-enyl)-2-n-pentyl-naphthalene,
6-(4-ethylcyclohex-1-enyl)-2-n-pentyl-naphthalene,
6-(4-n-propylcyclohex-1-enyl)-2-n-pentyl-naphthalene,
6-(4-n-butylcyclohex-1-enyl)-2-n-pentyl-naphthalene,
6-(4-n-pentylcyclohex-1-enyl)-2-n-pentyl-naphthalene,
6-(4-n-hexylcyclohex-1-enyl)-2-n-pentyl-naphthalene,
6-(4-n-heptylcyclohex-1-enyl)-2-n-pentyl-naphthalene,
6-(4-n-octylcyclohex-1-enyl)-2-n-pentyl-naphthalene,
6-[4-(2-methylbutyl)-cyclohex-1-enyl]-2-n-pentyl-naphthalene,
6-(4-methylcyclohex-1-enyl)-2-n-hexyl-naphthalene,
6-(4-ethylcyclohex-1-enyl)-2-n-hexyl-naphthalene,
6-(4-n-propylcyclohex-1-enyl)-2-n-hexyl-naphthalene,
6-(4-n-butylcyclohex-1-enyl)-2-n-hexyl-naphthalene,
6-(4-n-pentylcyclohex-1-enyl)-2-n-hexyl-naphthalene,
6-(4-n-hexylcyclohex-1-enyl)-2-n-hexyl-naphthalene,
6-(4-n-heptylcyclohex-1-enyl)-2-n-hexyl-naphthalene,
6-(4-n-octylcyclohex-1-enyl)-2-n-hexyl-naphthalene,
6-[4-(2-methylbutyl)-cyclohex-1-enyl]-2-n-hexyl-naphthalene,
6-(4-methylcyclohex-1-enyl)-2-n-heptyl-naphthalene,
6-(4-ethylcyclohex-1-enyl)-2-n-heptyl-naphthalene,
6-(4-n-propylcyclohex-1-enyl)-2-n-heptyl-naphthalene,
6-(4-n-butylcyclohex-1-enyl)-2-n-heptyl-naphthalene,
6-(4-n-pentylcyclohex-1-enyl)-2-n-heptyl-naphthalene,
6-(4-n-hexylcyclohex-1-enyl)-2-n-heptyl-naphthalene,
6-(4-n-heptylcyclohex-1-enyl)-2-n-heptyl-naphthalene,
6-[4-(2-methylbutyl)-cyclohex-1-enyl]-2-n-heptylnaphthalene,
6-(4-methylcyclohex-1-enyl)-2-n-octyl-naphthalene,
6-(4-ethylcyclohex-1-enyl)-2-n-octyl-naphthalene,
6-(4-n-propylcyclohex-1-enyl)-2-n-octyl-naphthalene,
6-(4-n-butylcyclohex-1-enyl)-2-n-octyl-naphthalene,
6-(4-n-pentylcyclohex-1-enyl)-2-n-octyl-naphthalene,
6-(4-n-hexylcyclohex-1-enyl)-2-n-octyl-naphthalene
and
6-[4-(2-methylbutyl)-cyclohex-1-enyl]-2-n-octyl-naphthalene.

EXAMPLE 2

154.5 g of 6-(4-n-hexylcyclohex-1-enyl)-2-n-hexyloxynaphthalene is dissolved in 1.5 l of ethyl acetate and hydrogenated under normal pressure for 48 hours in the presence of 50 g of palladium-on-carbon (5% of Pd). After filtering off the catalyst, the filtrate is evaporated.

The residue, together with 500 ml of dimethylsulfoxide and 50 g of potassium tert-butylate, is warmed to 83° for 20 hours and, after cooling down, poured onto 2.5 l of ice water; by repeated extraction with a total of 1 l of toluene, washing of the extracts with dilute hydrochloric acid and then with water, drying over sodium sulfate and evaporating, 6-(trans-4-n-hexylcyclohexyl)-2-n-hexyloxynaphthalene is obtained, which is recrystallized from acetone; m.p. 48°, c.p. 102°.

The following are prepared analogously:
6-(trans-4-methylcyclohexyl)-2-methoxy-naphthalene,
6-(trans-4-ethylcyclohexyl)-2-methoxy-naphthalene,
6-(trans-4-n-propylcyclohexyl)-2-methoxy naphthalene,
6-(trans-4-n-butylcyclohexyl)-2-methoxy-naphthalene,
6-(trans-4-n-pentylcyclohexyl)-2-methoxy-naphthalene,
6-(trans-4-n-hexylcyclohexyl)-2-methoxy-naphthalene,
6-(trans-4-n-heptylcyclohexyl)-2-methoxy-naphthalene,
6-(trans-4-n-octylcyclohexyl)-2-methoxy-naphthalene,
6-[trans-4-(2-methylbutyl)-cyclohexyl]-2-methoxynaphthalene,
6-(trans-4-methylcyclohexyl)-2-ethoxy-naphthalene,
6-(trans-4-ethylcyclohexyl)-2-ethoxy-naphthalene,
6-(trans-4-n-propylcyclohexyl)-2-ethoxy-naphthalene,
6-(trans-4-n-butylcyclohexyl)-2-ethoxy-naphthalene,
6-(trans-4-n-pentylcyclohexyl)-2-ethoxy-naphthalene,
6-(trans-4-n-hexylcyclohexyl)-2-ethoxy-naphthalene,
6-(trans-4-n-heptylcyclohexyl)-2-ethoxy-naphthalene,
6-(trans-4-n-octylcyclohexyl)-2-ethoxy-naphthalene,
6-[trans-4-(2-methylbutyl)-cyclohexyl]-2-ethoxynaphthalene,
6-(trans-4-methylcyclohexyl)-2-n-propoxy-naphthalene,
6-(trans-4-ethylcyclohexyl)-2-n-propoxy-naphthalene,
6-(trans-4-n-propylcyclohexyl)-2-n-propoxy-naphthalene,
6-(trans-4-n-butylcyclohexyl)-2-n-propoxy-naphthalene,
6-(trans-4-n-pentylcyclohexyl)-2-n-propoxy-naphthalene, m.p. 79°, c.p. 99°;
6-(trans-4-n-hexylcyclohexyl)-2-n-propoxy-naphthalene, 6-(trans-4-n-heptylcyclohexyl)-2-n-propoxy-naphthalene,
6-(trans-4-n-octylcyclohexyl)-2-n-propoxy-naphthalene,
6-[trans-4-(2-methylbutyl)-cyclohexyl]-2-n-propoxynaphthalene,
6-(trans-4-methylcyclohexyl)-2-n-butoxy-naphthalene,
6-(trans-4-ethylcyclohexyl)-2-n-butoxy-naphthalene,
6-(trans-4-n-propylcyclohexyl)-2-n-butoxy-naphthalene,
6-(trans-4-n-butylcyclohexyl)-2-n-butoxy-naphthalene,
6-(trans-4-n-pentylcyclohexyl)-2-n-butoxy-naphthalene, m.p. 58°, c.p. 103°;
6-(trans-4-n-hexylcyclohexyl)-2-n-butoxy-naphthalene,
6-(trans-4-n-heptylcyclohexyl)-2-n-butoxy-naphthalene,
6-(trans-4-n-octylcyclohexyl)-2-n-butoxy-naphthalene,
6-[trans-4-(2-methylbutyl)-cyclohexyl]-2-n-butoxynaphthalene,
6-(trans-4-methylcyclohexyl)-2-n-pentyloxy-naphthalene,
6-(trans-4-ethylcyclohexyl)-2-n-pentyloxy-naphthalene,
6-(trans-4-n-propylcyclohexyl)-2-n-pentyloxy-naphthalene,
6-(trans-4-n-butylcyclohexyl)-2-n-pentyloxy-naphthalene,
6-(trans-4-n-pentylcyclohexyl)-2-n-pentyloxy-naphthalene,
6-(trans-4-n-hexylcyclohexyl)-2-n-pentyloxy-naphthalene,
6-(trans-4-n-heptylcyclohexyl)-2-n-pentyloxy-naphthalene,
6-[trans-4-(2-methylbutyl)-cyclohexyl]-2-n-pentyloxynaphthalene,
6-(trans-4-methylcyclohexyl)-2-n-hexyloxy-naphthalene,
6-(trans-4-ethylcyclohexyl)-2-n-hexyloxy-naphthalene,
6-(trans-4-n-propylcyclohexyl)-2-n-hexyloxy-naphthalene,
6-(trans-4-n-butylcyclohexyl)-2-n-hexyloxy-naphthalene,
6-(trans-4-n-pentylcyclohexyl)-2-n-hexyloxy-naphthalene,
6-[trans-4-(2-methylbutyl)-cyclohexyl]-2-n-hexyloxynaphthalene,
6-(trans-4-methylcyclohexyl)-2-n-heptyloxy-naphthalene,
6-(trans-4-ethylcyclohexyl)-2-n-heptyloxy-naphthalene,
6-(trans-4-n-propylcyclohexyl)-2-n-heptyloxy-naphthalene,
6-(trans-4-n-butylcyclohexyl)-2-n-heptyloxy-naphthalene,
6-(trans-4-n-pentylcyclohexyl)-2-n-heptyloxy-naphthalene,
6-[trans-4-(2-methylbutyl)-cyclohexyl]-2-n-heptyloxynaphthalene,
6-(trans-4-methylcyclohexyl)-2-n-octyloxy-naphthalene,
6-(trans-4-ethylcyclohexyl)-2-n-octyloxy-naphthalene,
6-(trans-4-n-propylcyclohexyl)-2-n-octyloxy-naphthalene,
6-(trans-4-n-butylcyclohexyl)-2-n-octyloxy-naphthalene,
6-(trans-4-n-pentycyclohexyl)-2-n-octyloxy-naphthalene,
6-[trans-4-(2-methylbutyl)-cyclohexyl]-2-n-octyloxynaphthalene,
6-(trans-4-methylcyclohexyl)-2-methyl-naphthalene,
6-(trans-4-ethylcyclohexyl)-2-methyl-naphthalene,
6-(trans-4-n-propylcyclohexyl)-2-methyl-naphthalene,
6-(trans-4-n-butylcyclohexyl)-2-methyl-naphthalene,
6-(trans-4-n-pentylcyclohexyl)-2-methyl-naphthalene,
6-(trans-4-n-hexylcyclohexyl)-2-methyl-naphthalene,
6-(trans-4-n-heptylcyclohexyl)-2-methyl-naphthalene,
6-(trans-4-n-octylcyclohexyl)-2-methyl-naphthalene,
6-[trans-4-(2-methylbutyl)-cyclohexyl]-2-methylnaphthalene,
6-(trans-4-methylcyclohexyl)-2-ethyl-naphthalene,
6-(trans-4-ethylcyclohexyl)-2-ethyl-naphthalene,
6-(trans-4-n-propylcyclohexyl)-2-ethyl-naphthalene,
6-(trans-4-n-butylcyclohexyl)-2-ethyl-naphthalene,
6-(trans-4-n-pentylcyclohexyl)-2-ethyl-naphthalene,
6-(trans-4-n-hexylcyclohexyl)-2-ethyl-naphthalene,
6-(trans-4-n-heptylcyclohexyl)-2-ethyl-naphthalene,
6-(trans-4-n-octylcyclohexyl)-2-ethyl-naphthalene,
6-[trans-4-(2-methylbutyl)-cyclohexyl]-2-ethyl-naphthalene,
6-(trans-4-methylcyclohexyl)-2-n-propyl-naphthalene,
6-(trans-4-ethylcyclohexyl)-2-n-propyl-naphthalene,
6-(trans-4-n-propylcyclohexyl)-2-n-propyl-naphthalene,
6-(trans-4-n-butylcyclohexyl)-2-n-propyl-naphthalene,
6-(trans-4-n-pentylcyclohexyl)-2-n-propyl-naphthalene,
6-(trans-4-n-hexylcyclohexyl)-2-n-propyl-naphthalene,
6-(trans-4-n-heptylcyclohexyl)-2-n-propyl-naphthalene,
6-(trans-4-n-octylcyclohexyl)-2-n-propyl-naphthalene,
6-[trans-4-(2-methylbutyl)-cyclohexyl]-2-n-propylnaphthalene,
6-(trans-4-methylcyclohexyl)-2-n-butyl-naphthalene,
6-(trans-4-ethylcyclohexyl)-2-n-butyl-naphthalene,
6-(trans-4-n-propylcyclohexyl)-2-n-butyl-naphthalene,
6-(trans-4-n-butylcyclohexyl)-2-n-butyl-naphthalene,
6-(trans-4-n-pentylcyclohexyl)-2-n-butyl-naphthalene,
6-(trans-4-n-hexylcyclohexyl)-2-n-butyl-naphthalene,
6-(trans-4-n-heptylcyclohexyl)-2-n-butyl-naphthalene,
6-(trans-4-n-octylcyclohexyl)-2-n-butyl-naphthalene,
6-[trans-4-(2-methylbutyl)-cyclohexyl]-2-n-butylnaphthalene,
6-(trans-4-methylcyclohexyl)-2-n-pentyl-naphthalene,
6-(trans-4-ethylcyclohexyl)-2-n-pentyl-naphthalene,
6-(trans-4-n-propylcyclohexyl)-2-n-pentyl-naphthalene,
6-(trans-4-n-butylcyclohexyl)-2-n-pentyl-naphthalene,
6-(trans-4-n-pentylcyclohexyl)-2-n-pentyl-naphthalene,
6-(trans-4-n-hexylcyclohexyl)-2-n-pentyl-naphthalene,
6-(trans-4-n-heptylcyclohexyl)-2-n-pentyl-naphthalene,
6-(trans-4-n-octylcyclohexyl)-2-n-pentyl-naphthalene,
6-[trans-4-(2-methylbutyl)-cyclohexyl]-2-n-pentylnaphthalene,
6-(trans-4-methylcyclohexyl)-2-n-hexyl-naphthalene,
6-(trans-4-ethylcyclohexyl)-2-n-hexyl-naphthalene,
6-(trans-4-n-propylcyclohexyl)-2-n-hexyl-naphthalene,
6-(trans-4-n-butylcyclohexyl)-2-n-hexyl-naphthalene,
6-(trans-4-n-pentylcyclohexyl)-2-n-hexyl-naphthalene,
6-(trans-4-n-hexylcyclohexyl)-2-n-hexyl-naphthalene,
6-(trans-4-n-heptylcyclohexyl)-2-n-hexyl-naphthalene,
6-(trans-4-n-octylcyclohexyl)-2-n-hexyl-naphthalene,
6-[trans-4-(2-methylbutyl)-cyclohexyl]-2-n-hexylnaphthalene,
6-(trans-4-methylcyclohexyl)-2-n-heptyl-naphthalene,
6-(trans-4-ethylcyclohexyl)-2-n-heptyl-naphthalene,
6-(trans-4-n-propylcyclohexyl)-2-n-heptyl-naphthalene,
6-(trans-4-n-butylcyclohexyl)-2-n-heptyl-naphthalene,
6-(trans-4-n-pentylcyclohexyl)-2-n-heptyl-naphthalene,
6-(trans-4-n-hexylcyclohexyl)-2-n-heptyl-naphthalene,
6-(trans-4-n-heptylcyclohexyl)-2-n-heptyl-naphthalene,
6-[trans-4-(2-methylbutyl)-cyclohexyl]-2-n-heptylnaphthalene, 6-(trans-4-methylcyclohexyl)-2-n-octyl-naphthalene,
6-(trans-4-ethylcyclohexyl)-2-n-octyl-naphthalene,
6-(trans-4-n-propylcyclohexyl)-2-n-octyl-naphthalene,
6-(trans-4-n-butylcyclohexyl)-2-n-octyl-naphthalene,
6-(trans-4-n-pentylcyclohexyl)-2-n-octyl-naphthalene,
6-(trans-4-n-hexylcyclohexyl)-2-n-octyl-naphthalene and
6-[trans-4-(2-methylbutyl)-cyclohexyl]-2-n-octylnaphthalene.

EXAMPLE 3

(a) 23.8 g of 4-n-pentanoylbiphenyl and 3.0 g of paraformaldehyde are suspended in 70 ml of isopropyl alcohol and a solution of 0.6 g of potassium hydroxide in 3 ml of water is added to this suspension, with stirring. The reaction mixture is stirred for 10 hours at room temperature, then diluted with 250 ml of water and extracted with 300 ml of diethyl ether in 4 portions. The extracts are washed with water, dried over sodium sulfate and evaporated. 21.1 g of 1-(4-biphenylyl)-2-hydroxymethylpentan-1-one remains as an oily-crystalline mass which is processed further without further purification.

(b) 21.2 g of 1-(4-biphenylyl)-2-hydroxymethyl-pentan-1-one is dissolved in 300 ml of methanol and hydrogenated in the presence of 10 g of palladium-on-carbon (5% of Pd) at 30°, until the absorption of hydrogen ceases. After filtering off the catalyst, the solution is evaporated and the remaining 1-(4-biphenylyl)-2-hydroxymethylpentane is recrystallized from petroleum ether (boiling range 60°-80°); m.p. 60°.

(c) 4.6 g of phosphorus tribromide is added dropwise at room temperature, with stirring, to a solution of 12.5 g of 1-(4-biphenylyl)-2-hydroxymethylpentane in 40 ml of methylene chloride and the reaction mixture is then stirred for a further 1.5 hours. Subsequently, 40 ml of water is cautiously added with cooling, and the organic phase is then separated off, washed with 5% strength aqueous sodium bicarbonate solution and with water and dried over calcium chloride. After distilling off the methylene chloride, 14.3 g of 1-(4-biphenylyl)-2-bromomethyl-pentane remains as an oily residue which is further processed without further purification.

(d) 14.3 g of 1-(4-biphenylyl)-2-bromomethyl-pentane is introduced at 60°, with stirring, into a suspension of 2.6 g of sodium cyanide in 25 ml of dimethylsulfoxide. The reaction mixture is then stirred for 2 hours at 70°, 125 ml of water is added after cooling and the mixture is extracted with 200 ml of diethyl ether. The extract is extracted by shaking with 10 ml of 20% strength aqueous hydrochloric acid, washed with water, dried over calcium chloride and evaporated. 9.4 g of 3-n-propyl-4-(4-biphenylyl)-butyronitrile remains as a yellowish oily liquid.

(e) 9.4 g of 3-n-propyl-4-(4-biphenylyl)-butyronitrile is heated to the boil under reflux for 10 hours with a solution of 2.8 g of sodium hydroxide in 12 ml of water. After cooling, the reaction mixture is extracted by shaking with 10 ml of methylene chloride and the aqueous phase is then acidified with 5% strength aqueous hydrochloric acid, while cooling with ice. The 3-n-propyl-4-(4-biphenylyl)-butyric acid, which separates out as an oil, is extracted with diethyl ether, and the extract is washed with water, dried over calcium chloride and evaporated; 5.3 g of 3-n-propyl-4-(4-biphenylyl)-butyric acid remains in an oily-crystalline form.

(f) 5.3 g of 3-n-propyl-4-(4-biphenylyl)-butyric acid is added slowly, with stirring, to 15 g of polyphosphoric acid which has been heated to 145°, and the reaction mixture is then heated to 145° for a further 3 minutes. While still liquid, the mixture is poured onto 100 g of ice and the aqueous mixture is extracted with 100 ml of diethyl ether. The extract is washed with 5% strength aqueous sodium bicarbonate solution and with water, dried over sodium sulfate and evaporated. This gives a residue of 3.6 g of 3-n-propyl-7-phenyl-1,2,3,4-tetrahydronaphthalen-1-one. This is dissolved in 25 ml of methanol and hydrogenated at 30° in the presence of 1 g of palladium-on-carbon (5% of Pd), until the absorption of hydrogen ceases. After filtering off the catalyst and distilling off the solvent, 3.0 g of 6-phenyl-2-n-propyl-1,2,3,4-tetrahydronaphthalene remains.

The following are prepared analogously:
6-phenyl-2-methyl-1,2,3,4-tetrahydronaphthalene,
6-phenyl-2-ethyl-1,2,3,4-tetrahydronaphthalene,
6-phenyl-2-n-butyl-1,2,3,4-tetrahydronaphthalene,
6-phenyl-2-n-pentyl-1,2,3,4-tetrahydronaphthalene,
6-phenyl-2-n-hexyl-1,2,3,4-tetrahydronaphthalene,
6-phenyl-2-n-heptyl-1,2,3,4-tetrahydronaphthalene,
6-phenyl-2-n-octyl-1,2,3,4-tetrahydronaphthalene, and
6-phenyl-2-(2-methylbutyl)-1,2,3,4-tetrahydronaphthalene.

(g) 11.2 g of n-butyryl chloride and then a solution of 25.1 g of 6-phenyl-2-n-propyl-1,2,3,4-tetrahydronaphthalene in 40 ml of trichloroethylene are added dropwise, while stirring and cooling with ice, to a suspension of 16.0 g of aluminum chloride in 40 ml of trichloroethylene in such a way that the temperature does not rise above 20°. Subsequently, the reaction mixture is stirred for a further 1 hour, then left to stand for 15 hours and finally poured onto a mixture of 1 kg of ice and 100 ml of 35% strength aqueous hydrochloric acid. The organic phase is separated off, washed with 2% strength aqueous sodium hydroxide solution and with water and dried over calcium chloride. After distilling off the solvent and recrystallizing from ethanol, 29.7 g of 6-(4-n-butyrylphenyl)-2-n-propyl-1,2,3,4-tetrahydronaphthalene remains.

(h) 29.7 g of 6-(4-n-butyrylphenyl)-2-n-propyl-1,2,3,4-tetrahydronaphthalene is dissolved in 200 ml of methanol and hydrogenated at 30° and under normal pressure in the presence of 10 g of palladium-on-carbon (5% of Pd), until the absorption of hydrogen ceases. After filtering off the catalyst, the solvent is distilled off and the remaining 6-(4-n-butylphenyl)-2-n-propyl-1,2,3,4-tetrahydronaphthalene is recrystallized from ethanol; yield 21.5 g.

The following are prepared analogously:
6-(4-ethylphenyl)-2-methyl-1,2,3,4-tetrahydronaphthalene,
6-(4-ethylphenyl)-2-ethyl-1,2,3,4-tetrahydronaphthalene,
6-(4-ethylphenyl)-2-n-propyl-1,2,3,4-tetrahydronaphthalene,
6-(4-ethylphenyl)-2-n-butyl-1,2,3,4-tetrahydronaphthalene,
6-(4-ethylphenyl)-2-n-pentyl-1,2,3,4-tetrahydronaphthalene,
6-(4-ethylphenyl)-2-n-hexyl-1,2,3,4-tetrahydronaphthalene,
6-(4-ethylphenyl)-2-n-heptyl-1,2,3,4-tetrahydronaphthalene,
6-(4-ethylphenyl)-2-n-octyl-1,2,3,4-tetrahydronaphthalene,
6-(4-ethylphenyl)-2-(2-methylbutyl)-1,2,3,4-tetrahydronaphthalene, 6-(4-n-propylphenyl)-2-methyl-1,2,3,4-tetrahydronaphthalene,
6-(4-n-propylphenyl)-2-ethyl-1,2,3,4-tetrahydronaphthalene,
6-(4-n-propylphenyl)-2-n-propyl-1,2,3,4-tetrahydronaphthalene,
6-(4-n-propylphenyl)-2-n-butyl-1,2,3,4-tetrahydronaphthalene,
6-(4-n-propylphenyl)-2-n-pentyl-1,2,3,4-tetrahydronaphthalene,
6-(4-n-propylphenyl)-2-n-hexyl-1,2,3,4-tetrahydronaphthalene,
6-(4-n-propylphenyl)-2-n-heptyl-1,2,3,4-tetrahydronaphthalene,
6-(4-n-propylphenyl)-2-n-octyl-1,2,3,4-tetrahydronaphthalene,
6-(4-n-propylphenyl)-2-(2-methylbutyl)-1,2,3,4-tetrahydronaphthalene,
6-(4-n-butylphenyl)-2-methyl-1,2,3,4-tetrahydronaphthalene,
6-(4-n-butylphenyl)-2-ethyl-1,2,3,4-tetrahydronaphthalene,
6-(4-n-butylphenyl)-2-n-butyl-1,2,3,4-tetrahydronaphthalene,
6-(4-n-butylphenyl)-2-n-pentyl-1,2,3,4-tetrahydronaphthalene,
6-(4-n-butylphenyl)-2-n-hexyl-1,2,3,4-tetrahydronaphthalene,
6-(4-n-butylphenyl)-2-n-heptyl-1,2,3,4-tetrahydronaphthalene,
6-(4-n-butylphenyl)-2-n-octyl-1,2,3,4-tetrahydronaphthalene,
6-(4-n-butylphenyl)-2-(2-methylbutyl)-1,2,3,4-tetrahydronaphthalene,
6-(4-n-pentylphenyl)-2-methyl-1,2,3,4-tetrahydronaphthalene,
6-(4-n-pentylphenyl)-2-ethyl-1,2,3,4-tetrahydronaphthalene,
6-(4-n-pentylphenyl)-2-n-propyl-1,2,3,4-tetrahydronaphthalene,
6-(4-n-pentylphenyl)-2-n-butyl-1,2,3,4-tetrahydronaphthalene,
6-(4-n-pentylphenyl)-2-n-pentyl-1,2,3,4-tetrahydronaphthalene,
6-(4-n-pentylphenyl)-2-n-hexyl-1,2,3,4-tetrahydronaphthalene,
6-(4-n-pentylphenyl)-2-n-heptyl-1,2,3,4-tetrahydronaphthalene,
6-(4-n-pentylphenyl)-2-n-octyl-1,2,3,4-tetrahydronaphthalene,
6-(4-n-pentylphenyl)-2-(2-methylbutyl)-1,2,3,4-tetrahydronaphthalene,
6-(4-n-hexylphenyl)-2-methyl-1,2,3,4-tetrahydronaphthalene,
6-(4-n-hexylphenyl)-2-ethyl-1,2,3,4-tetrahydronaphthalene,
6-(4-n-hexylphenyl)-2-n-propyl-1,2,3,4-tetrahydronaphthalene,
6-(4-n-hexylphenyl)-2-n-butyl-1,2,3,4-tetrahydronaphthalene,
6-(4-n-hexylphenyl)-2-n-pentyl-1,2,3,4-tetrahydronaphthalene,
6-(4-n-hexylphenyl)-2-n-hexyl-1,2,3,4-tetrahydronaphthalene,
6-(4-n-hexylphenyl)-2-n-heptyl-1,2,3,4-tetrahydronaphthalene,
6-(4-n-hexylphenyl)-2-(2-methylbutyl)-1,2,3,4-tetrahydronaphthalene,
6-(4-n-heptylphenyl)-2-methyl-1,2,3,4-tetrahydronaphthalene,
6-(4-n-heptylphenyl)-2-ethyl-1,2,3,4-tetrahydronaphthalene,
6-(4-n-heptylphenyl)-2-n-propyl-1,2,3,4-tetrahydronaphthalene,
6-(4-n-heptylphenyl)-2-n-butyl-1,2,3,4-tetrahydronaphthalene,
6-(4-n-heptylphenyl)-2-n-pentyl-1,2,3,4-tetrahydronaphthalene,
6-(4-n-heptylphenyl)-2-n-hexyl-1,2,3,4-tetrahydronaphthalene,
6-(4-n-heptylphenyl)-2-(2-methylbutyl)-1,2,3,4-tetrahydronaphthalene,
6-(4-n-octylphenyl)-2-methyl-1,2,3,4-tetrahydronaphthalene,
6-(4-n-octylphenyl)-2-ethyl-1,2,3,4-tetrahydronaphthalene,
6-(4-n-octylphenyl)-2-n-propyl-1,2,3,4-tetrahydronaphthalene,
6-(4-n-octylphenyl)-2-n-butyl-1,2,3,4-tetrahydronaphthalene,
6-(4-n-octylphenyl)-2-n-pentyl-1,2,3,4-tetrahydronaphthalene,
6-(4-n-octylphenyl)-2-n-hexyl-1,2,3,4-tetrahydronaphthalene,
6-(4-n-octylphenyl)-2-(2-methylbutyl)-1,2,3,4-tetrahydronaphthalene,
6-[4-(2-methylbutyl)-phenyl]-2-n-propyl-1,2,3,4-tetrahydronaphthalene,
6-[4-(2-methylbutyl)-phenyl]-2-n-butyl-1,2,3,4-tetrahydronaphthalene,
6-[4-(2-methylbutyl)-phenyl]-2-n-pentyl-1,2,3,4-tetrahydronaphthalene,
6-[4-(2-methylbutyl)-phenyl]-2-n-hexyl-1,2,3,4-tetrahydronaphthalene,
6-[4-(2-methylbutyl)-phenyl]-2-n-heptyl-1,2,3,4-tetrahydronaphthalene and
6-[4-(2-methylbutyl)-phenyl]-2-n-octyl-1,2,3,4-tetrahydronaphthalene.

EXAMPLE 4

29.2 g of 6-(4-acetylphenyl)-2-n-propyl-1,2,3,4-tetrahydronaphthalene (prepared analogously to Example 3g) is dissolved in a mixture of 300 ml of methylene chloride and 300 ml of formic acid, and 18 ml of 30% strength aqueous hydrogen peroxide solution is added, with stirring, to the above solution at the boiling point. The reaction mixture is stirred for 16 hours at a bath temperature of 50° and then concentrated to a volume of 160 ml. The residue is diluted with an equal amount of water, and the 6-(4-acetoxyphenyl)-2-n-propyl-1,2,3,4-tetrahydronaphthalene, which crystallized out on cooling, is filtered off and recrystallized from petroleum ether (boiling range 60°-80°).

The following are prepared analogously:
6-(4-acetoxyphenyl)-2-methyl-1,2,3,4-tetrahydronaphthalene,
6-(4-acetoxyphenyl)-2-ethyl-1,2,3,4-tetrahydronaphthalene,
6-(4-acetoxyphenyl)-2-n-butyl-1,2,3,4-tetrahydronaphthalene,
6-(4-acetoxyphenyl)-2-n-pentyl-1,2,3,4-tetrahydronaphthalene,
6-(4-acetoxyphenyl)-2-n-hexyl-1,2,3,4-tetrahydronaphthalene,
6-(4-acetoxyphenyl)-2-n-heptyl-1,2,3,4-tetrahydronaphthalene, 6-(4-acetoxyphenyl)-2-n-octyl-1,2,3,4-tetrahydronaphthalene and 6-(4-acetoxyphenyl)-2-(2-methylbutyl)-1,2,3,4-tetrahydronaphthalene.

EXAMPLE 5

(a) 30.8 g of 6-(4-acetoxyphenyl)-2-n-propyl-1,2,3,4-tetrahydronaphthalene is heated to the boil, for 3 hours, with 110 ml of 2 N sodium hydroxide solution and 50 ml of ethanol. Subsequently, the ethanol is distilled off and the aqueous residue is acidified with dilute hydrochloric acid (pH 3), while cooling with ice. The 6-(4-hydroxyphenyl)-2-n-propyl-1,2,3,4-tetrahydronaphthalene, which precipitates, is filtered off and recrystallized from methanol; yield 23 g.

(b) A solution of 13.3 g of 6-(4-hydroxyphenyl)-2-n-propyl-1,2,3,4-tetrahydronaphthalene in 70 ml of dimethylformamide is heated for 10 hours to 100°, while stirring, with 7 g of n-butyl bromide and 7 g of potassium carbonate. After cooling, the reaction mixture is filtered, the filtrate is evaporated, the residue is taken up in 70 ml of diethyl ether and the solution is washed with water and dried over sodium sulfate. After distilling off the diethyl ether, 14.8 g of 6-(4-n-butoxyphenyl)-2-n-propyl-1,2,3,4-tetrahydronaphthalene remains, and is recrystallized from methanol.

The following are prepared analogously:

6-(4-methoxyphenyl)-2-methyl-1,2,3,4-tetrahydronaphthalene,
6-(4-methoxyphenyl)-2-ethyl-1,2,3,4-tetrahydronaphthalene,
6-(4-methoxyphenyl)-2-n-propyl-1,2,3,4-tetrahydronaphthalene,
6-(4-methoxyphenyl)-2-n-butyl-1,2,3,4-tetrahydronaphthalene,
6-(4-methoxyphenyl)-2-n-pentyl-1,2,3,4-tetrahydronaphthalene,
6-(4-methoxyphenyl)-2-n-hexyl-1,2,3,4-tetrahydronaphthalene,
6-(4-methoxyphenyl)-2-n-heptyl-1,2,3,4-tetrahydronaphthalene,
6-(4-methoxyphenyl)-2-n-octyl-1,2,3,4-tetrahydronaphthalene,
6-(4-methoxyphenyl)-2-(2-methylbutyl)-1,2,3,4-tetrahydronaphthalene,
6-(4-ethoxyphenyl)-2-methyl-1,2,3,4-tetrahydronaphthalene,
6-(4-ethoxyphenyl)-2-ethyl-1,2,3,4-tetrahydronaphthalene,
6-(4-ethoxyphenyl)-2-n-propyl-1,2,3,4-tetrahydronaphthalene,
6-(4-ethoxyphenyl)-2-n-butyl-1,2,3,4-tetrahydronaphthalene,
6-(4-ethoxyphenyl)-2-n-pentyl-1,2,3,4-tetrahydronaphthalene,
6-(4-ethoxyphenyl)-2-n-hexyl-1,2,3,4-tetrahydronaphthalene,
6-(4-ethoxyphenyl)-2-n-heptyl-1,2,3,4-tetrahydronaphthalene,
6-(4-ethoxyphenyl)-2-n-octyl-1,2,3,4-tetrahydronaphthalene,
6-(4-ethoxyphenyl)-2-(2-methylbutyl)-1,2,3,4-tetrahydronaphthalene,
6-(4-n-propoxyphenyl)-2-methyl-1,2,3,4-tetrahydronaphthalene,
6-(4-n-propoxyphenyl)-2-ethyl-1,2,3,4-tetrahydronaphthalene,
6-(4-n-propoxyphenyl)-2-n-propyl-1,2,3,4-tetrahydronaphthalene,
6-(4-n-propoxyphenyl)-2-n-butyl-1,2,3,4-tetrahydronaphthalene,
6-(4-n-propoxyphenyl)-2-n-pentyl-1,2,3,4-tetrahydronaphthalene,
6-(4-n-propoxyphenyl)-2-n-hexyl-1,2,3,4-tetrahydronaphthalene,
6-(4-n-propoxyphenyl)-2-n-heptyl-1,2,3,4-tetrahydronaphthalene,
6-(4-n-propoxyphenyl)-2-n-octyl-1,2,3,4-tetrahydronaphthalene,
6-(4-n-propoxyphenyl)-2-(2-methylbutyl)-1,2,3,4-tetrahydronaphthalene,
6-(4-n-butoxyphenyl)-2-methyl-1,2,3,4-tetrahydronaphthalene,
6-(4-n-butoxyphenyl)-2-ethyl-1,2,3,4-tetrahydronaphthalene,
6-(4-n-butoxyphenyl)-2-n-butyl-1,2,3,4-tetrahydronaphthalene,
6-(4-n-butoxyphenyl)-2-n-pentyl-1,2,3,4-tetrahydronaphthalene,
6-(4-n-butoxyphenyl)-2-n-hexyl-1,2,3,4-tetrahydronaphthalene,
6-(4-n-butoxyphenyl)-2-n-heptyl-1,2,3,4-tetrahydronaphthalene,
6-(4-n-butoxyphenyl)-2-n-octyl-1,2,3,4-tetrahydronaphthalene,
6-(4-n-butoxyphenyl)-2-(2-methylbutyl)-1,2,3,4-tetrahydronaphthalene,
6-(4-n-pentyloxyphenyl)-2-methyl-1,2,3,4-tetrahydronaphthalene,
6-(4-n-pentyloxyphenyl)-2-ethyl-1,2,3,4-tetrahydronaphthalene,
6-(4-n-pentyloxyphenyl)-2-n-propyl-1,2,3,4-tetrahydronaphthalene,
6-(4-n-pentyloxyphenyl)-2-n-butyl-1,2,3,4-tetrahydronaphthalene,
6-(4-n-pentyloxyphenyl)-2-n-pentyl-1,2,3,4-tetrahydronaphthalene,
6-(4-n-pentyloxyphenyl)-2-n-hexyl-1,2,3,4-tetrahydronaphthalene,
6-(4-n-pentyloxyphenyl)-2-n-heptyl-1,2,3,4-tetrahydronaphthalene,
6-(4-n-pentyloxyphenyl)-2-n-octyl-1,2,3,4-tetrahydronaphthalene,
6-(4-n-pentyloxyphenyl)-2-(2-methylbutyl)-1,2,3,4-tetrahydronaphthalene,
6-(4-n-hexyloxyphenyl)-2-methyl-1,2,3,4-tetrahydronaphthalene,
6-(4-n-hexyloxyphenyl)-2-ethyl-1,2,3,4-tetrahydronaphthalene,
6-(4-n-hexyloxyphenyl)-2-n-propyl-1,2,3,4-tetrahydronaphthalene,
6-(4-n-hexyloxyphenyl)-2-n-butyl-1,2,3,4-tetrahydronaphthalene,
6-(4-n-hexyloxyphenyl)-2-n-pentyl-1,2,3,4-tetrahydronaphthalene,
6-(4-n-hexyloxyphenyl)-2-n-hexyl-1,2,3,4-tetrahydronaphthalene,
6-(4-n-hexyloxyphenyl)-2-n-heptyl-1,2,3,4-tetrahydronaphthalene,
6-(4-n-hexyloxyphenyl)-2-n-octyl-1,2,3,4-tetrahydronaphthalene,
6-(4-n-hexyloxyphenyl)-2-(2-methylbutyl)-1,2,3,4-tetrahydronaphthalene,
6-(4-n-heptyloxyphenyl)-2-methyl-1,2,3,4-tetrahydronaphthalene, 6-(4-n-heptyloxyphenyl)-2-ethyl-1,2,3,4-tetrahydronaphthalene,
6-(4-n-heptyloxyphenyl)-2-n-propyl-1,2,3,4-tetrahydronaphthalene,
6-(4-n-heptyloxyphenyl)-2-n-butyl-1,2,3,4-tetrahydronaphthalene,
6-(4-n-heptyloxyphenyl)-2-n-pentyl-1,2,3,4-tetrahydronaphthalene,
6-(4-n-heptyloxyphenyl)-2-n-hexyl-1,2,3,4-tetrahydronaphthalene,
6-(4-n-heptyloxyphenyl)-2-(2-methylbutyl)-1,2,3,4-tetrahydronaphthalene,
6-(4-n-octyloxyphenyl)-2-methyl-1,2,3,4-tetrahydronaphthalene,
6-(4-n-octyloxyphenyl)-2-ethyl-1,2,3,4-tetrahydronaphthalene,
6-(4-n-octyloxyphenyl)-2-n-propyl-1,2,3,4-tetrahydronaphthalene,
6-(4-n-octyloxyphenyl)-2-n-butyl-1,2,3,4-tetrahydronaphthalene,
6-(4-n-octyloxyphenyl)-2-n-pentyl-1,2,3,4-tetrahydronaphthalene,
6-(4-n-octyloxyphenyl)-2-n-hexyl-1,2,3,4-tetrahydronaphthalene and
6-(4-n-octyloxyphenyl)-2-(2-methylbutyl)-1,2,3,4-tetrahydronaphthalene.

EXAMPLE 6

A solution of 5.5 g of n-butyryl chloride in 25 ml of pyridine is added dropwise, with stirring, to a solution of 13.3 g of 6-(4-hydroxyphenyl)-2-n-propyl-1,2,3,4-tetrahydronaphthalene in 75 ml of pyridine. The reaction mixture is heated to the boil under reflux for 2 hours and, after cooling, 100 ml of diethyl ether is added first and then 100 ml of water is added. After thorough shaking, the organic phase is separated off and the aqueous phase is once more extracted by shaking with 50 ml of diethyl ether; the combined organic phases are washed with water, dried over sodium sulfate and evaporated. The remaining 6-(4-n-butyryloxyphenyl)-2-n-propyl-1,2,3,4-tetrahydronaphthalene is recrystallized from ethanol.

The following are prepared analogously:
6-(4-propionyloxyphenyl)-2-methyl-1,2,3,4-tetrahydronaphthalene,
6-(4-propionyloxyphenyl)-2-ethyl-1,2,3,4-tetrahydronaphthalene,
6-(4-propionyloxyphenyl)-2-n-propyl-1,2,3,4-tetrahydronaphthalene,
6-(4-propionyloxyphenyl)-2-n-butyl-1,2,3,4-tetrahydronaphthalene,
6-(4-propionyloxyphenyl)-2-n-pentyl-1,2,3,4-tetrahydronaphthalene,
6-(4-propionyloxyphenyl)-2-n-hexyl-1,2,3,4-tetrahydronaphthalene,
6-(4-propionyloxyphenyl)-2-n-heptyl-1,2,3,4-tetrahydronaphthalene,
6-(4-propionyloxyphenyl)-2-n-octyl-1,2,3,4-tetrahydronaphthalene,
6-(4-propionyloxyphenyl)-2-(2-methylbutyl)-1,2,3,4-tetrahydronaphthalene,
6-(4-n-butyryloxyphenyl)-2-methyl-1,2,3,4-tetrahydronaphthalene,
6-(4-n-butyryloxyphenyl)-2-ethyl-1,2,3,4-tetrahydronaphthalene,
6-(4-n-butyryloxyphenyl)-2-n-butyl-1,2,3,4-tetrahydronaphthalene,
6-(4-n-butyryloxyphenyl)-2-n-pentyl-1,2,3,4-tetrahydronaphthalene,
6-(4-n-butyryloxyphenyl)-2-n-hexyl-1,2,3,4-tetrahydronaphthalene,
6-(4-n-butyryloxyphenyl)-2-n-heptyl-1,2,3,4-tetrahydronaphthalene,
6-(4-n-butyryloxyphenyl)-2-n-octyl-1,2,3,4-tetrahydronaphthalene,
6-(4-n-butyryloxyphenyl)-2-(2-methylbutyl)-1,2,3,4-tetrahydronaphthalene,
6-(4-pentanoyloxyphenyl)-2-methyl-1,2,3,4-tetrahydronaphthalene,
6-(4-n-pentanoyloxyphenyl)-2-ethyl-1,2,3,4-tetrahydronaphthalene,
6-(4-n-pentanoyloxyphenyl)-2-n-propyl-1,2,3,4-tetrahydronaphthalene,
6-(4-n-pentanoyloxyphenyl)-2-n-butyl-1,2,3,4-tetrahydronaphthalene,
6-(4-n-pentanoyloxyphenyl)-2-n-pentyl-1,2,3,4-tetrahydronaphthalene,
6-(4-n-pentanoyloxyphenyl)-2-n-hexyl-1,2,3,4-tetrahydronaphthalene,
6-(4-n-pentanoyloxyphenyl)-2-n-heptyl-1,2,3,4-tetrahydronaphthalene,
6-(4-n-pentanoyloxyphenyl)-2-n-octyl-1,2,3,4-tetrahydronaphthalene,
6-(4-n-pentanoyloxyphenyl)-2-(2-methylbutyl)-1,2,3,4-tetrahydronaphthalene,
6-(4-n-hexanoyloxyphenyl)-2-methyl-1,2,3,4-tetrahydronaphthalene,
6-(4-n-hexanoyloxyphenyl)-2-ethyl-1,2,3,4-tetrahydronaphthalene,
6-(4-n-hexanoyloxyphenyl)-2-n-propyl-1,2,3,4-tetrahydronaphthalene,
6-(4-n-hexanoyloxyphenyl)-2-n-butyl-1,2,3,4-tetrahydronaphthalene,
6-(4-n-hexanoyloxyphenyl)-2-n-pentyl-1,2,3,4-tetrahydronaphthalene,
6-(4-n-hexanoyloxyphenyl)-2-n-hexyl-1,2,3,4-tetrahydronaphthalene,
6-(4-n-hexanoyloxyphenyl)-2-n-heptyl-1,2,3,4-tetrahydronaphthalene,
6-(4-n-hexanoyloxyphenyl)-2-n-octyl-1,2,3,4-tetrahydronaphthalene,
6-(4-n-hexanoyloxyphenyl)-2-(2-methylbutyl)-1,2,3,4-tetrahydronaphthalene,
6-(4-n-heptanoyloxyphenyl)-2-methyl-1,2,3,4-tetrahydronaphthalene,
6-(4-n-heptanoyloxyphenyl)-2-ethyl-1,2,3,4-tetrahydronaphthalene,
6-(4-n-heptanoyloxyphenyl)-2-n-propyl-1,2,3,4-tetrahydronaphthalene,
6-(4-n-heptanoyloxyphenyl)-2-n-butyl-1,2,3,4-tetrahydronaphthalene,
6-(4-n-heptanoyloxyphenyl)-2-n-pentyl-1,2,3,4-tetrahydronaphthalene,
6-(4-n-heptanoyloxyphenyl)-2-n-hexyl-1,2,3,4-tetrahydronaphthalene,
6-(4-n-heptanoyloxyphenyl)-2-(2-methylbutyl)-1,2,3,4-tetrahydronaphthalene,
6-(4-n-octanoyloxyphenyl)-2-methyl-1,2,3,4-tetrahydronaphthalene,
6-(4-n-octanoyloxyphenyl)-2-ethyl-1,2,3,4-tetrahydronaphthalene,
6-(4-n-octanoyloxyphenyl)-2-n-propyl-1,2,3,4-tetrahydronaphthalene,
6-(4-n-octanoyloxyphenyl)-2-n-butyl-1,2,3,4-tetrahydronaphthalene, 6-(4-n-octanoyloxyphenyl)-2-n-pentyl-1,2,3,4-tetrahydronaphthalene, 6-(4-n-octanoyloxyphenyl)-2-n-hexyl-1,2,3,4-tetrahydronaphthalene and 6-(4-n-octanoyloxyphenyl)-2-(2-methylbutyl)-1,2,3,4-tetrahydronaphthalene.

EXAMPLE 7

17.6 g of bromine is added dropwise, with stirring and cooling to −10°, to a solution of 27.8 g of 6-phenyl-2-n-pentyl-1,2,3,4-tetrahydronaphthalene in 100 ml of methylene chloride. The reaction mixture is then stirred for a further 20 hours at room temperature and washed with water, 5% strength aqueous sodium bicarbonate solution and water, dried over calcium chlor and evaporated. The remaining 6-(4-bromophenyl)-2-n-pentyl-1,2,3,4-tetrahydronaphthalene is recrystallized from methanol; yield 27.2 g.

The following are prepared analogously:

6-(4-bromophenyl)-2-methyl-1,2,3,4-tetrahydronaphthalene, 6-(4-bromophenyl)-2-ethyl-1,2,3,4-tetrahydronaphthalene, 6-(4-bromophenyl)-2-n-propyl-1,2,3,4-tetrahydronaphthalene, 6-(4-bromophenyl)-2-n-butyl-1,2,3,4-tetrahydronaphthalene, 6-(4-bromophenyl)-2-n-hexyl-1,2,3,4-tetrahydronaphthalene, 6-(4-bromophenyl)-2-n-heptyl-1,2,3,4-tetrahydronaphthalene, 6-(4-bromophenyl)-2-n-octyl-1,2,3,4-tetrahydronaphthalene, 6-(4-bromophenyl)-2-(2-methylbutyl)-1,2,3,4-tetrahydronaphthalene.

EXAMPLE 8

35.7 g of 6-(4-bromophenyl)-2-n-pentyl-1,2,3,4-tetrahydronaphthalene and 9 g of copper-(I) cyanide are heated in 100 ml of N-methylpyrrolidone to 190°–200° for 18 hours, with stirring. After cooling to 50°, the reaction mixture is poured onto 1,000 ml of ice water. The precipitate thus separating out if filtered off and, after drying, extracted with several times 50 ml of methylene chloride. The aqueous filtrate is likewise extracted with 100 ml of methylene chloride. The combined extracts are washed with water, dried over sodium sulfate and evaporated. The remaining 6-(4-cyanophenyl)-2-n-pentyl-1,2,3,4-tetrahydronaphthalene is recrystallized from ethanol: yield 24.5 g.

The following are prepared analogously:

6-(4-cyanophenyl)-2-methyl-1,2,3,4-tetrahydronaphthalene, 6-(4-cyanophenyl)-2-ethyl-1,2,3,4-tetrahydronaphthalene, m.p. 82.3°, c.p. 81.6°, 6-(4cyanophenyl)-2-n-propyl-1,2,3,4-tetrahydronaphthalene, 6-(4-cyanophenyl)-2-n-butyl-1,2,3,4-tetrahydronaphthalene, 6-(4-cyanophenyl)-2-n-hexyl-1,2,3,4-tetrahydronaphthalene, 6-(4-cyanophenyl)-2-n-heptyl-1,2,3,4-tetrahydronaphthalene, 6-(4-cyanophenyl)-2-n-octyl-1,2,3,4-tetrahydronaphthalene, 6-(4-cyanophenyl)-2-(2-methylbutyl)-1,2,3,4-tetrahydronaphthalene.

EXAMPLE 9

(a) A suspension of 8.2 g of 6-(4-cyanophenyl)-2-n-heptyl-1,2,3,4-tetrahydronaphthalene in a solution of 2 g of sodium hydroxide in 12 ml of water is heated to the boil under reflux for 10 hours. After cooling, the reaction mixture is extracted once with 10 ml of methylene chloride and then acidified with 5% strength aqueous hydrochloric acid. The acidified mixture is extracted twice with 30 ml of diethyl ether and, after drying over sodium sulfate, the extracts are evaporated. The remaining 4-(2-n-heptyl-1,2,3,4-tetrahydronaphth-6-yl)-benzoic acid is heated to the boil for 2 hours with 10 ml of thionyl chloride. After distilling off excess thionyl chloride, 7.4 g of 4-(2-n-heptyl-1,2,3,4-tetrahydronaphth-6-yl)-benzoyl chloride remains, and this is heated in a sealed tube with 4.2 g of phosphorus pentachloride for 24 hours to 180°. After cooling, the reaction mixture is poured into 100 ml of ice water, and 50 ml of 2 N sodium hydroxide solution is added. The alkaline solution is extracted by shaking twice with 50 ml of methylene chloride; the organic phases are washed with water, dried over calcium chloride and evaporated. The remaining 6-(4-trichloromethylphenyl)-2-n-heptyl-1,2,3,4-tetrahydronaphthalene is recrystallized from a mixture of equal parts by volume of cyclohexane and ethyl acetate; yield 4.7 g.

(b) 4.7 g of 6-(4-trichloromethylphenyl)-2-n-heptyl-1,2,3,4-tetrahydronaphthalene is heated to 130°, and 2.2 g of antimony trifluoride is added over the course of 20 minutes. After a further 5 minutes, the reaction mixture is allowed to cool and is poured into 40 ml of a mixture of equal parts of ice and concentrated hydrochloric acid. The aqueous reaction mixture is extracted twice with 40 ml of deithyl ether; the extracts are washed with 5% strength aqueous sodium bicarbonate solution and with water, dired over sodium sulfate and evaporated. The remaining 6-(4-trifluoromethylphenyl)-2-n-heptyl-1,2,3,4-tetrahydronaphthalene is recrystallized from methanol; yield 3.54 g.

The following are prepared analogously:

6-(4-trifluoromethylphenyl)-2-methyl-1,2,3,4-tetrahydronaphthalene, 6-(4-trifluoromethylphenyl)-2-ethyl-1,2,3,4-tetrahydronaphthalene, 6-(4-trifluoromethylphenyl)-2-n-propyl-1,2,3,4-tetrahydronaphthalene, 6-(4-trifluoromethylphenyl)-2-n-butyl-1,2,3,4-tetrahydronaphthalene, 6-(4-trifluoromethylphenyl)-2-n-pentyl-1,2,3,4-tetrahydronaphthalene, 6-(4-trifluoromethylphenyl)-2-n-hexyl-1,2,3,4-tetrahydronaphthalene, 6-(4-trifluoromethylphenyl)-2-n-octyl-1,2,3,4-tetrahydronaphthalene, and 6-(4-trifluoromethylphenyl)-2-(2-methylbutyl)-1,2,3,4-tetrahydronaphthalene.

EXAMPLE 10

Analogously to Example 3(a)–(f) and starting from the corresponding 4-(trans-4-alkylcyclohexyl)-phenones, the following 6-(trans-4-alkylcyclohexyl)-2-alkyl-1,2,3,4-tetrahydronaphthalenes are prepared:

6-(4-trans-methylcyclohexyl)-2-methyl-1,2,3,4-tetrahydronaphthalene, 6-(4-trans-methylcyclohexyl)-2-ethyl-1,2,3,4-tetrahydronaphthalene, 6-(4-trans-methylcyclohexyl)-2-n-propyl-1,2,3,4-tetrahydronaphthalene,
6-(4-trans-methylcyclohexyl)-2-n-butyl-1,2,3,4-tetrahydronaphthalene,
6-(4-trans-methylcyclohexyl)-2-n-pentyl-1,2,3,4-tetrahydronaphthalene,
6-(4-trans-methylcyclohexyl)-2-n-hexyl-1,2,3,4-tetrahydronaphthalene,
6-(4-trans-methylcyclohexyl)-2-n-heptyl-1,2,3,4-tetrahydronaphthalene,
6-(4-trans-methylcyclohexyl)-2-n-octyl-1,2,3,4-tetrahydronaphthalene,
6-(4-trans-methylcyclohexyl)-2-(2-methylbutyl)-1,2,3,4-tetrahydronaphthalene,
6-(4-trans-ethylcyclohexyl)-2-methyl-1,2,3,4-tetrahydronaphthalene,
6-(4-trans-ethylcyclohexyl)-2-ethyl-1,2,3,4-tetrahydronaphthalene,
6-(4-trans-ethylcyclohexyl)-2-n-propyl-1,2,3,4-tetrahydronaphthalene,
6-(4-trans-ethylcyclohexyl)-2-n-butyl-1,2,3,4-tetrahydronaphthalene,
6-(4-trans-ethylcyclohexyl)-2-n-pentyl-1,2,3,4-tetrahydronaphthalene,
6-(4-trans-ethylcyclohexyl)-2-n-hexyl-1,2,3,4-tetrahydronaphthalene,
6-(4-trans-ethylcyclohexyl)-2-n-heptyl-1,2,3,4-tetrahydronaphthalene,
6-(4-trans-ethylcyclohexyl)-2-n-octyl-1,2,3,4-tetrahydronaphthalene,
6-(4-trans-ethylcyclohexyl)-2-(2-methylbutyl)-1,2,3,4-tetrahydronaphthalene,
6-(4-trans-n-propylcyclohexyl)-2-methyl-1,2,3,4-tetrahydronaphthalene,
6-(4-trans-n-propylcyclohexyl)-2-ethyl-1,2,3,4-tetrahydronaphthalene,
6-(4-trans-n-propylcyclohexyl)-2-n-propyl-1,2,3,4-tetrahydronaphthalene,
6-(4-trans-n-propylcyclohexyl)-2-n-butyl-1,2,3,4-tetrahydronaphthalene,
6-(4-trans-n-propylcyclohexyl)-2-n-pentyl-1,2,3,4-tetrahydronaphthalene,
6-(4-trans-n-propylcyclohexyl)-2-n-hexyl-1,2,3,4-tetrahydronaphthalene,
6-(4-trans-n-propylcyclohexyl)-2-n-heptyl-1,2,3,4-tetrahydronaphthalene,
6-(4-trans-n-propylcyclohexyl)-2-n-octyl-1,2,3,4-tetrahydronaphthalene,
6-(4-trans-n-propylcyclohexyl)-2-(2-methylbutyl)-1,2,3,4-tetrahydronaphthalene,
6-(4-trans-n-butylcyclohexyl)-2-methyl-1,2,3,4-tetrahydronaphthalene,
6-(4-trans-n-butylcyclohexyl)-2-ethyl-1,2,3,4-tetrahydronaphthalene,
6-(4-trans-n-butylcyclohexyl)-2-n-propyl-1,2,3,4-tetrahydronaphthalene,
6-(4-trans-n-butylcyclohexyl)-2-n-butyl-1,2,3,4-tetrahydronaphthalene,
6-(4-trans-n-butylcyclohexyl)-2-n-pentyl-1,2,3,4-tetrahydronaphthalene,
6-(4-trans-n-butylcyclohexyl)-2-n-hexyl-1,2,3,4-tetrahydronaphthalene,
6-(4-trans-n-butylcyclohexyl)-2-n-heptyl-1,2,3,4-tetrahydronaphthalene,
6-(4-trans-n-butylcyclohexyl)-2-n-octyl-1,2,3,4-tetrahydronaphthalene,
6-(4-trans-n-butylcyclohexyl)-2-(2-methylbutyl)-1,2,3,4-tetrahydronaphthalene,
6-(4-trans-n-pentylcyclohexyl)-2-methyl-1,2,3,4-tetrahydronaphthalene,
6-(4-trans-n-pentylcyclohexyl)-2-ethyl-1,2,3,4-tetrahydronaphthalene,
6-(4-trans-n-pentylcyclohexyl)-2-n-propyl-1,2,3,4-tetrahydronaphthalene,
6-(4-trans-n-pentylcyclohexyl)-2-n-butyl-1,2,3,4-tetrahydronaphthalene,
6-(4-trans-n-pentylcyclohexyl)-2-n-pentyl-1,2,3,4-tetrahydronaphthalene,
6-(4-trans-n-pentylcyclohexyl)-2-n-hexyl-1,2,3,4-tetrahydronaphthalene,
6-(4-trans-n-pentylcyclohexyl)-2-n-heptyl-1,2,3,4-tetrahydronaphthalene,
6-(4-trans-n-pentylcyclohexyl)-2-n-octyl-1,2,3,4-tetrahydronaphthalene,
6-(4-trans-n-pentylcyclohexyl)-2-(2-methylbutyl)-1,2,3,4-tetrahydronaphthalene,
6-(4-trans-n-hexylcyclohexyl)-2-methyl-1,2,3,4-tetrahydronaphthalene,
6-(4-trans-n-hexylcyclohexyl)-2-ethyl-1,2,3,4-tetrahydronaphthalene,
6-(4-trans-n-hexylcyclohexyl)-2-n-propyl-1,2,3,4-tetrahydronaphthalene,
6-(4-trans-n-hexylcyclohexyl)-2-n-butyl-1,2,3,4-tetrahydronaphthalene,
6-(4-trans-n-hexylcyclohexyl)-2-n-pentyl-1,2,3,4-tetrahydronaphthalene,
6-(4-trans-n-hexylcyclohexyl)-2-n-hexyl-1,2,3,4-tetrahydronaphthalene,
6-(4-trans-n-hexylcyclohexyl)-2-n-heptyl-1,2,3,4-tetrahydronaphthalene,
6-(4-trans-n-hexylcyclohexyl)-2-n-octyl-1,2,3,4-tetrahydronaphthalene,
6-(4-trans-n-hexylcyclohexyl)-2-(2-methylbutyl)-1,2,3,4-tetrahydronaphthalene,
6-(4-trans-n-heptylcyclohexyl)-2-methyl-1,2,3,4-tetrahydronaphthalene,
6-(4-trans-n-heptylcyclohexyl)-2-ethyl-1,2,3,4-tetrahydronaphthalene,
6-(4-trans-n-heptylcyclohexyl)-2-n-propyl-1,2,3,4-tetrahydronaphthalene,
6-(4-trans-n-heptylcyclohexyl)-2-n-butyl-1,2,3,4-tetrahydronaphthalene,
6-(4-trans-n-heptylcyclohexyl)-2-n-pentyl-1,2,3,4-tetrahydronaphthalene,
6-(4-trans-n-heptylcyclohexyl)-2-n-hexyl-1,2,3,4-tetrahydronaphthalene,
6-(4-trans-n-heptylcyclohexyl)-2-(2-methylbutyl)-1,2,3,4-tetrahydronaphthalene,
6-(4-trans-n-octylcyclohexyl)-2-methyl-1,2,3,4-tetrahydronaphthalene,
6-(4-trans-n-octylcyclohexyl)-2-ethyl-1,2,3,4-tetrahydronaphthalene,
6-(4-trans-n-octylcyclohexyl)-2-n-propyl-1,2,3,4-tetrahydronaphthalene and
6-(4-trans-n-octylcyclohexyl)-2-n-butyl-1,2,3,4-tetrahydronaphthalene.

EXAMPLE 11

(a) A mixture of 4.0 g of 6-(4-n-hexylcyclohex-1-enyl)-2-benzyloxynaphthalene (prepared analogously to Example 1, starting from 6-bromo-2-benzyloxynaphthalene) and 3.5 g of pyridine hydrochloride is heated to 200°–220° for 1 hour. After cooling, the reaction mixture is poured into 100 ml of water and the suspension thus obtained is extracted three times with 50 ml of diethyl ether. The combined organic phases are dried over sodium sulfate and evaporated, finally under reduced pressure. The remaining 6-(4-n-hexylcyclohex-1-enyl)-2-naphthol is recrystallized from methanol; yield 2.1 g of colorless crystals.

(b) 0.5 g of n-butyryl chloride is added at 100° to a solution of 1.5 g of 6-(4-n-hexylcyclohex-1-enyl)-2-naphthol and 0.4 g of pyridine in 50 ml of toluene. The reaction mixture is heated to 100° for a further 2 hours and is then filtered and evaporated. The remaining 6-(4-n-hexylcyclohex-1-enyl)-2-n-butyryloxynaphthalene is recrystallized from ethanol.

The following are prepared analogously:
6-(4-methylcyclohex-1-enyl)-2-acetoxy-naphthalene,
6-(4-ethylcyclohex-1-enyl)-2-acetoxy-naphthalene,
6-(4-n-propylcyclohex-1-enyl)-2-acetoxy-naphthalene,
6-(4-n-butylcyclohex-1-enyl)-2-acetoxy-naphthalene,
6-(4-n-pentylcyclohex-1-enyl)-2-acetoxy-naphthalene,
6-(4-n-hexylcyclohex-1-enyl)-2-acetoxy-naphthalene,
6-(4-n-heptylcyclohex-1-enyl)-2-acetoxy-naphthalene,
6-(4-n-octylcyclohex-1-enyl)-2-acetoxy-naphthalene,
6-[4-(2-methylbutyl)-cyclohex-1-enyl]-2-acetoxy-naphthalene,
6-(4-methylcyclohex-1-enyl)-2-propionyloxy-naphthalene,
6-(4-ethylcyclohex-1-enyl)-2-propionyloxy-naphthalene,
6-(4-n-propylcyclohex-1-enyl)-2-propionyloxy-naphthalene,
6-(4-n-butylcyclohex-1-enyl)-2-propionyloxy-naphthalene,
6-(4-n-pentylcyclohex-1-enyl)-2-propionyloxy-naphthalene,
6-(4-n-hexylcyclohex-1-enyl)-2-propionyloxy-naphthalene,
6-(4-n-heptylcyclohex-1-enyl)-2-propionyloxy-naphthalene,
6-(4-n-octylcyclohex-1-enyl)-2-propionyloxy-naphthalene,
6-[4-(2-methylbutyl)-cyclohex-1-enyl]-2-propionyloxy-naphthalene,
6-(4-methylcyclohex-1-enyl)-2-n-butyryloxy-naphthalene,
6-(4-ethylcyclohex-1-enyl)-2-n-butyryloxy-naphthalene,
6-(4-n-propylcyclohex-1-enyl)-2-n-butyryloxy-naphthalene,
6-(4-n-butylcyclohex-1-enyl)-2-n-butyryloxy-naphthalene,
6-(4-n-pentylcyclohex-1-enyl)-2-n-butyryloxy-naphthalene,
6-(4-n-heptylcyclohex-1-enyl)-2-n-butyryloxy-naphthalene,
6-(4-n-octylcyclohex-1-enyl)-2-n-butyryloxy-naphthalene,
6-[4-(2-methylbutyl)-cyclohex-1-enyl]-2-n-butyryloxy-naphthalene,
6-(4-methylcyclohex-1-enyl)-2-n-pentanoyloxy-naphthalene,
6-(4-ethylcyclohex-1-enyl)-2-n-pentanoyloxy-naphthalene,
6-(4-n-propylcyclohex-1-enyl)-2-n-pentanoyloxy-naphthalene,
6-(4-n-butylcyclohex-1-enyl)-2-n-pentanoyloxy-naphthalene,
6-(4-n-pentylcyclohex-1-enyl)-2-n-pentanoyloxy-naphthalene,
6-(4-n-hexylcyclohex-1-enyl)-2-n-pentanoyloxy-naphthalene,
6-(4-n-heptylcyclohex-1-enyl)-2-n-pentanoyloxy-naphthalene,
6-(4-n-octylcyclohex-1-enyl)-2-n-pentanoyloxy-naphthalene,
6-[4-(2-methylbutyl)-cyclohex-1-enyl]-2-n-pentanoyloxy-naphthalene,
6-(4-methylcyclohex-1-enyl)-2-n-hexanoyloxy-naphthalene,
6-(4-ethylcyclohex-1-enyl)-2-n-hexanoyloxy-naphthalene,
6-(4-n-propylcyclohex-1-enyl)-2-n-hexanoyloxy-naphthalene,
6-(4-n-butylcyclohex-1-enyl)-2-n-hexanoyloxy-naphthalene,
6-(4-n-pentylocyclohex-1-enyl)-2-n-hexanoyloxy-naphthalene,
6-(4-n-hexylcyclohex-1-enyl)-2-n-hexanoyloxy-naphthalene,
6-(4-n-heptylcyclohex-1-enyl)-2-n-hexanoyloxy-naphthalene,
6-(4-n-octylcyclohex-1-enyl)-2-n-hexanoyloxy-naphthalene,
6-[4-(2-methylbutyl)-cyclohex-1-enyl]-2-n-hexanoyloxy-naphthalene,
6-(4-methylcyclohex-1-enyl)-2-n-heptanoyloxy-naphthalene,
6-(4-ethylcyclohex-1-enyl)-2-n-heptanoyloxy-naphthalene,
6-(4-n-propylcyclohex-1-enyl)-2-n-heptanoyloxy-naphthalene,
6-(4-n-butylcyclohex-1-enyl)-2-n-heptanoyloxy-naphthalene,
6-(4-n-pentylcyclohex-1-enyl)-2-n-heptanoyloxy-naphthalene,
6-(4-n-hexylcyclohex-1-enyl)-2-n-heptanoyloxy-naphthalene and
6-[4-(2-methylbutyl)-cyclohex-1-enyl]-2-n-heptanoyloxy-naphthalene.

EXAMPLE 12

3.4 g of 2,6-dibromonaphthalene is added dropwise over the course of half an hour, at 35°–40°, to 3.0 g of magnesium in 20 ml of tetrahydrofuran. The reaction mixture is stirred for a further hour at room temperature, and 1.4 g of 4-n-hexylcyclohexanone is then added dropwise over the course of 10 minutes. After stirring for a further hour at room temperature, 25 ml of 6 N hydrochloric acid is added dropwise; the reaction mixture obtained is extracted four times with 50 ml of n-hexane. The combined organic phases are dried over sodium sulfate and evaporated. The residue is taken up in 20 ml of acetone and heated to the boil under reflux for 2 hours with 0.5 g of p-toluene-sulfonic acid. Subsequently, the reaction mixture is cooled to −10°, and the 6-(4-n-hexylcyclohex-1-enyl)-2-bromonaphthalene which has crystallized out is filtered off and recrystallized once from acetone; yield 3.1 g.

The following are prepared analogously:
6-(4-methylcyclohex-1-enyl)-2-bromonaphthalene,
6-(4-ethylcyclohex-1-enyl)-2-bromonaphthalene,
6-(4-n-propylcyclohex-1-enyl)-2-bromonaphthalene,
6-(4-n-butylcyclohex-1-enyl)-2-bromonaphthalene,
6-(4-n-pentylcyclohex-1-enyl)-2-bromonaphthalene,
6-(4-n-heptylcyclohex-1-enyl)-2-bromonaphthalene,
6-(4-n-octylcyclohex-1-enyl)-2-bromonaphthalene, and
6-[4-(2-methylbutyl)-cyclohex-1-enyl]-2-bromonaphthalene.

EXAMPLE 13

3.1 g of 6-(4-n-hexylcyclohex-1-enyl)-2-bromonaphthalene and 3.0 g of copper-(I) cyanide are heated in 20 ml of N-methylpyrrolidone for 8 hours at 195°. After cooling, the reaction mixture is poured into 100 ml of water and the precipitate thus forming is filtered off. The precipitate is taken up in hot toluene and the suspension obtained is filtered. The filtrate is evaporated and the remaining 6-(4-n-hexyl-cyclohex-1-enyl)-2-cyanonaphthalene is recrystallized from acetone; yield 1.8 g of colorless crystals.

The following are prepared analogously:
6-(4-methylcyclohex-1-enyl)-2-cyanonaphthalene,
6-(4-ethylcyclohex-1-enyl)-2-cyanonaphthalene,
6-(4-n-propylcyclohex-1-enyl)-2-cyanonaphthalene,
6-(4-n-butylcyclohex-1-enyl)-2-cyanonaphthalene,
6-(4-n-pentylcyclohex-1-enyl)-2-cyanonaphthalene,
6-(4-n-heptylcyclohex-1-enyl)-2-cyanonaphthalene,
6-(4-n-octylcyclohex-1-enyl)-2-cyanonaphthalene, and
6-[4-(2-methylbutyl)-cyclohex-1-enyl]-2-cyclonaphthalene.

EXAMPLE 14

(a) A mixture of 11.7 g of 6-(trans-4-n-propylcyclohexyl)-2-benzyloxynaphthalene (prepared by hydrogenation of 6-(4-n-propylcyclohex-1-enyl)-2-benzyloxynaphthalene with the calculated quantity of hydrogen over platinum oxide in ethyl acetate, under normal pressure and at room temperature), 6.5 g of trimethylchlorosilane and 9 g of sodium iodide is warmed in 30 ml of acetonitrile to 50°-75° for 6 hours. Subsequently, the reaction mixture is filtered and 50 ml of water is added to the filtrate. The aqueous reaction mixture obtained is evaporated under reduced pressure and the remaining 6-(trans-4-n-propylcyclohexyl)-2-naphthol is recrystallized from methanol; yield 8.6 g.

(B) Analogously to Example 11(b), the following are prepared from the corresponding 6-(trans-4-alkylcyclohexyl)-2-naphthols:
6-(trans-4-methylcyclohexyl)-2-acetoxy-naphthalene,
6-(trans-4-ethylcyclohexyl)-2-acetoxy-naphthalene,
6-(trans-4-n-propylcyclohexyl)-2-acetoxy-naphthalene,
6-(trans-4-n-butylcyclohexyl)-2-acetoxy-naphthalene,
6-(trans-4-n-pentylcyclohexyl)-2-acetoxy-naphthalene,
6-(trans-4-n-hexylcyclohexyl)-2-acetoxy-naphthalene,
6-(trans-4-n-heptylcyclohexyl)-2-acetoxy-naphthalene,
6-(trans-4-n-octylcyclohexyl)-2-acetoxy-naphthalene,
6-[trans-4-(2-methylbutyl)-cyclohexyl]-2-acetoxy-naphthalene,
6-(trans-4-methylcyclohexyl)-2-propionyloxy-naphthalene,
6-(trans-4-ethylcyclohexyl)-2-propionyloxy-naphthalene,
6-(trans-4-n-propylcyclohexyl)-2-propionyloxy-naphthalene,
6-(trans-4-n-butylcyclohexyl)-2-propionyloxy-naphthalene,
6-(trans-4-n-pentylcyclohexyl)-2-propionyloxy-naphthalene,
6-(trans-4-n-hexylcyclohexyl)-2-propionyloxy-naphthalene,
6-(trans-4-n-heptylcyclohexyl)-2-propionyloxy-naphthalene,
6-(trans-4-n-octylcyclohexyl)-2-propionyloxy-naphthalene,
6-[trans-4-(2-methylbutyl)-cyclohexyl]-2-propionyloxy-naphthalene,
6-(trans-4-methylcyclohexyl)-2-n-butyryloxy-naphthalene,
6-(trans-4-ethylcyclohexyl)-2-n-butyryloxy-naphthalene,
6-(trans-4-n-propylcyclohexyl)-2-n-butyryloxy-naphthalene,
6-(trans-4-n-butylcyclohexyl)-2-n-butyryloxy-naphthalene,
6-(trans-4-n-hexylcyclohexyl)-2-n-butyryloxy-naphthalene,
6-(trans-4-n-heptylcyclohexyl)-2-n-butyryloxy-naphthalene,
6-(trans-4-n-octylcyclohexyl)-2-n-butyryloxy-naphthalene,
6-[trans-4-(2-methylbutyl)-cyclohexyl]-2-n-butyryloxy-naphthalene,
6-(trans-4-methylcyclohexyl)-2-n-pentanoyloxy-naphthalene,
6-(trans-4-ethylcyclohexyl)-2-n-pentanoyloxy-naphthalene,
6-(trans-4-n-propylcyclohexyl)-2-n-pentanoyloxy-naphthalene,
6-(trans-4-n-butylcyclohexyl)-2-n-pentanoyloxy-naphthalene,
6-(trans-4-n-pentylcyclohexyl)-2-n-pentanoyloxy-naphthalene,
6-(trans-4-n-hexylcyclohexyl)-2-n-pentanoyloxy-naphthalene,
6-(trans-4-n-heptylcyclohexyl)-2-n-pentanoyloxy-naphthalene,
6-(trans-4-n-octylcyclohexyl)-2-n-pentanoyloxy-naphthalene,
6-[trans-4-(2-methylbutyl)-cyclohexyl]-2-n-pentanoyloxy-naphthalene,
6-(trans-4-methylcyclohexyl)-2-n-hexanoyloxy-naphthalene,
6-(trans-4-ethylcyclohexyl)-2-n-hexanoyloxy-naphthalene,
6-(trans-4-n-propylcyclohexyl)-2-n-hexanoyloxy-naphthalene,
6-(trans-4-n-butylcyclohexyl)-2-n-hexanoyloxy-naphthalene,
6-(trans-4-n-pentylcyclohexyl)-2-n-hexanoyloxy-naphthalene,
6-(trans-4-n-hexylcyclohexyl)-2-n-hexanoyloxy-naphthalene,
6-(trans-4-n-heptylcyclohexyl)-2-n-hexanoyloxy-naphthalene,
6-(trans-4-n-octylcyclohexyl)-2-n-hexanoyloxy-naphthalene,
6-[trans-4-(2-methylbutyl)-cyclohexyl]-2-n-hexanoyloxynaphthalene,
6-(trans-4-methylcyclohexyl)-2-n-heptanoyloxy-naphthalene,
6-(trans-4-ethylcyclohexyl)-2-n-heptanoyloxy-naphthalene,
6-(trans-4-n-propylcyclohexyl)-2-n-heptanoyloxy-naphthalene,
6-(trans-4-n-butylcyclohexyl)-2-n-heptanoyloxy-naphthalene,
6-(trans-4-n-pentylcyclohexyl)-2-n-heptanoyloxy-naphthalene,
6-(trans-4-n-hexylcyclohexyl)-2-n-heptanoyloxy-naphthalene, and
6-[trans-4-(2-methylbutyl)-cyclohexyl]-2-n-heptanoyloxy-naphthalene.

EXAMPLE 15

4.4 g of bromine is first added dropwise, with cooling, to a solution of 7.2 g of triphenylphosphine in 13 ml of acetonitrile and a solution of 6.8 g of 6-(trans-4-n-propylcyclohexyl)-2-naphthol in 25 ml of acetonitrile is then added dropwise at room temperature. The reaction mixture is warmed to 70° for 30 minutes and then evaporated, and the residue is heated to 370° for 30 minutes. After cooling, the solid residue is extracted four times with 50 ml of hexane and the combined extracts are purified by filtration over a 15 cm long column of neutral alumina. After evaporation of the filtrate, 4.5 g of 6-(trans-4-n-propylcyclohexyl)-2-bromonaphthalene remains in the form of colorless crystals.

The following are prepared analogously:
6-(trans-4-methylcyclohexyl)-2-bromonaphthalene,
6-(trans-4-ethylcyclohexyl)-2-bromonaphthalene,
6-(trans-4-n-butylcyclohexyl)-2-bromonaphthalene,
6-(trans-4-n-pentylcyclohexyl)-2-bromonaphthalene,
6-(trans-4-n-hexylcyclohexyl)-2-bromonaphthalene,
6-(trans-4-n-heptylcyclohexyl)-2-bromonaphthalene,
6-(trans-4-n-octylcyclohexyl)-2-bromonaphthalene, and
6-[trans-4-(2-methylbutyl)-cyclohexyl]-2-bromonaphthalene.

EXAMPLE 16

Analogously to Example 13, the following are prepared from the 6-(trans-4-alkylcyclohexyl)-2-bromonaphthalenes prepared in accordance with Example 15:
6-(trans-4-methylcyclohexyl)-2-cyanonaphthalene,
6-(trans-4-ethylcyclohexyl)-2-cyclonaphthalene,
6-(trans-4-n-propylcyclohexyl)-2-cyanonaphthalene,
6-(trans-4-n-butylcyclohexyl)-2-cyanonaphthalene,
6-(trans-4-n-pentylcyclohexyl)-2-cyanonaphthalene,
6-(trans-4-n-hexylcyclohexyl)-2-cyanonaphthalene,
6-(trans-4-n-heptylcyclohexyl)-2-cyanonaphthalene,
6-(trans-4-n-octylcyclohexyl)-2-cyanonaphthalene, and
6[trans-4-(2-methylbutyl)-cyclohexyl]-2-cyanonaphthalene.

EXAMPLE 17

Analogously to Example 9, the following are prepared from the 6-(trans-4-alkylcyclohexyl)-2-cyanonaphthalenes prepared in accordance with Example 16:
6-(trans-4-methylcyclohexyl)-2-trifluoromethylnaphthalene,
6-(trans-4-ethylcyclohexyl)-2-trifluoromethylnaphthalene,
6-(trans-4-n-propylcyclohexyl)-2-trifluoromethylnaphthalene,
6-(trans-4-n-butylcyclohexyl)-2-trifluoromethylnaphthalene,
6-(trans-4-n-pentylcyclohexyl)-2-trifluoromethylnaphthalene,
6-(trans-4-n-hexylcyclohexyl)-2-trifluoromethylnaphthalene,
6-(trans-4-n-heptylcyclohexyl)-2-trifluoromethylnaphthalene,
6-(trans-4-n-octylcyclohexyl)-2-trifluoromethylnaphthalene, and
6-[trans-4-(2-methylbutyl)-cyclohexyl]-2-trifluoromethylnaphthalene.

The following examples relate to the use of the naphthalene derivatives of this invention as components of liquid-crystalline dielectrics.

EXAMPLE 18

A mixture of 40 parts by weight of 4-(trans-4-n-propylcyclohexyl)-benzonitrile and 60 parts by weight of 4-(trans-4-n-pentylcyclohexyl)-benzonitrile has a nematic phase in the temperature range from +8° to +51°. A liquid-crystalline dielectric which represents a ternary eutectic having a nematic phase in the temperature range from −1° to +66° is obtained by adding 33 parts by weight of 6-(trans-4-n-hexylcyclohexyl)-2-n-hexyloxy-naphthalene.

EXAMPLE 19

A mixture of 55 parts by weight of 4'-n-propylphenyl 4-n-hexanoyloxybenzoate and 45 parts by weight of 4'-n-heptylphenyl 4-n-hexanoyloxybenzoate has a nematic phase in the temperature range from +20° to +57° and a dielectric anisotropy of −0.5. A liquid-crystalline dielectric which is a ternary eutectic having a nematic phase in the temperature range from +8° to 69° and a dielectric anisotropy of −0.7 is obtained by adding 25 parts by weight of 6-(trans-4-n-pentylcyclohexyl)-2-n-butoxynaphthalene. This dielectric is very suitable for electro-optical display elements, the operation of which is based on the phenomenon of dynamic scattering.

EXAMPLE 20

A mixture of 29 parts by weight of 4-(trans-4-n-propylcyclohexyl)-benzonitrile, 41 parts by weight of 4-(trans-4-n-pentylcyclohexyl)-benzonitrile and 30 parts by weight of 4-(trans-4-n-heptylcyclohexyl)-benzonitrile has a nematic phase in the temperature range from −3° to +52° and an optical anisotropy of +0.12. A liquid-crystalline dielectric which shows a nematic phase in the temperature range from −7° to +65° C. and an optical anisotropy of +0.14 is obtained by adding 11 parts by weight of 6-(4-n-propylcyclohex-1-enyl)-2-n-butoxynaphthalene and 10 parts by weight of 6-(4-n-pentylcyclohex-1-enyl)-2-n-butoxynaphthalene. Due to the greater optical anisotropy, the possibility of interference colors appearing in electro-optical display elements, having an irregular layer thickness of the liquid-crystalline dielectric, is reduced.

EXAMPLE 21

A mixture of 67 parts by weight of 4-n-pentylphenyl anisate and 33 parts by weight of 4'-n-pentylphenyl 4-n-hexyloxybenzoate has a nematic phase in the temperature range from +15° to +48°. A liquid-crystalline dielectric which represents a ternary eutectic having a nematic phase in the temperature range from +7° to +58° is obtained by adding 20 parts by weight of 6-(trans-4-n-pentylcyclohexyl)-2-n-propoxynaphthalene.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:
1. A naphthalene derivative of the formula

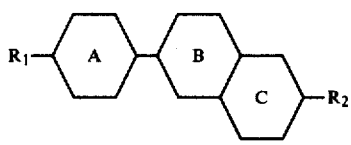

wherein ring A is 1,4-phenylene and ring system BC is 3,4-dihydro-2,6-naphthylene or 1,2,3,4-tetrahydro-2,6-naphthylene; and $R_1$ is alkyl, alkoxy, or alkanoyloxy having up to 8 C atoms in each case, CN, or halogen; and $R_2$ is attached to the 2 position of ring system BC and is alkyl of up to 8 C atoms.

2. A naphthalene derivative of claim 1, wherein $R_1$ and $R_2$ contain a straight-chain alkyl moiety.

3. A liquid-crystalline dielectric, comprising two liquid-crystalline components, at least one of which is a naphthalene derivative of claim 1.

4. An electro-optical display element comprising a liquid-crystal cell, wherein the liquid-crystalline cell contains a liquid-crystalline dielectric of claim 3.

* * * * *